(12) United States Patent
Yoshioka et al.

(10) Patent No.: US 6,337,089 B1
(45) Date of Patent: Jan. 8, 2002

(54) MICROCAPSULE CONTAINING CORE MATERIAL AND METHOD FOR PRODUCING THE SAME

(75) Inventors: Masato Yoshioka; Akihiro Segawa; Emi Segawa; Koji Nosaka; Terumi Yoshihara; Takashi Adachi; Hiroshi Shintani; Yuka Ueda, all of Osaka (JP)

(73) Assignee: Seiwa Kasei Company, Limited, Osaka (JP)

( * ) Notice: Subject to any disclaimer, the term of this patent is extended or adjusted under 35 U.S.C. 154(b) by 0 days.

(21) Appl. No.: 09/245,285

(22) Filed: Feb. 5, 1999

(30) Foreign Application Priority Data

Feb. 6, 1998 (JP) .............................................. 10-41063
Oct. 29, 1998 (JP) ............................................ 10-322933

(51) Int. Cl.$^7$ ............................ A61K 9/48; A61K 9/00; A61K 9/14; A61K 9/16; A61K 9/50

(52) U.S. Cl. ...................... 424/451; 424/400; 424/489; 424/490; 424/497; 424/501

(58) Field of Search ............................... 424/400, 489, 424/490, 497, 501, 451

(56) References Cited

U.S. PATENT DOCUMENTS

| | | | |
|---|---|---|---|
| 3,257,330 A | | 6/1966 | Burzynski et al. |
| 3,551,346 A | | 12/1970 | Breen et al. |
| 4,169,069 A | | 9/1979 | Unger et al. |
| 4,370,160 A | * | 1/1983 | Ziemelis |
| 4,931,362 A | * | 6/1990 | Zsifkovits et al. |
| 4,985,166 A | | 1/1991 | Leising et al. |
| 5,108,636 A | | 4/1992 | Leising et al. |
| 5,296,569 A | | 3/1994 | Noda et al. |
| 5,387,622 A | * | 2/1995 | Yamamoto |
| 5,455,048 A | * | 10/1995 | Lahmani et al. |

FOREIGN PATENT DOCUMENTS

| | | |
|---|---|---|
| DE | 2925305 A1 | 1/1980 |
| DE | 19741581 A1 | 4/1998 |
| EP | 0271979 | 6/1988 |
| EP | 0304416 A1 | 2/1989 |
| FR | 2091482 A | 1/1972 |
| JP | 5849433 A | 3/1983 |
| JP | 5184909 A | 7/1993 |
| JP | 6099272 B2 | 12/1994 |
| JP | 7504115 A | 5/1995 |
| JP | 2251240 A | 2/1999 |

\* cited by examiner

*Primary Examiner*—Thurman K. Page
*Assistant Examiner*—S. Tran
(74) *Attorney, Agent, or Firm*—Birch, Stewart, Kolasch & Birch, LLP

(57) ABSTRACT

A microcapsule containing core material and a capsule wall, in which the capsule wall of the microcapsule comprises:

organopolysiloxane synthesized by polycondensing one or more compounds represented by the general formula (II):

$$R_n Si(OH)_m Y_{(4-m-n)} \qquad (II)$$

wherein, m represents an integer from 1 to 4; n represents an integer from 0 to 3; $m+n \leq 4$; R represents an organic group in which a carbon atom is directly connected to a silicone atom, and when n is greater than 1, each of the R groups may be the same or different; and Y represents at least one group selected from the group consisting of an alkoxy group, hydrogen and siloxy group, and when (4−m−n) is greater than 1, each of the groups Y may be the same or different; provided that the compound (B) comprises at least one compound of formula(II) wherein m=2 or 3 and at least one of R group possesses affinity for at least one of a continuous phase and a dispersed phase;

a method for producing the microcapsule; and a use of the microcapseile, for example for cosmetics are provided.

14 Claims, No Drawings

MICROCAPSULE CONTAINING CORE MATERIAL AND METHOD FOR PRODUCING THE SAME

BACKGROUND OF THE INVENTION

1. Field of the Invention

The present invention relates to a microcapsule that contains a core material and a method for producing the same. More particularly, the present invention relates to a microcapsule, which has a capsule wall composed of organopolysiloxane obtained by polycondensation of a specific hydroxysilane, having thermal and mechanical stability and light resistance and which is bio-inactive.

The microcapsule of the present invention is applied, for example, to pharmaceuticals, liquid crystal, chemical products, recording materials, cosmetic compositions, aromatics, enzymes, agriculture, adhesives, fiber, foods, catalysts, detergents, dyes, paints, preservatives, solvents and the like. Specific examples thereof include microcapsules containing aspirin, vitamins or liquid crystals, pressure sensitive manifold paper, a capsule containing ultraviolet ray absorbers, coloring matters, pigments, aromatics, menthol, insecticides or adhesives, a capsule containing a preservative for rivet, and the like, although use of the microcapsule is not limited to the above-mentioned uses.

2. Description of the Related Art

Application of organopolysiloxanes in a wide range of fields is expected since they have excellent properties such as thermal and mechanical stability and light resistance, and bio-inactivity and the like as general basic properties. Also in the field of microcapsules, such as a microcapsule in the narrow sense and a nanocapsule, production of microcapsules has been previously tried using a capsule walls composed of a polysiloxane or an analogous material.

For example, U.S. Pat. No. 3,257,330 discloses a method for producing a colored gel particle comprising organopolysiloxane as a matrix. However, when an alkoxysilane having a hydrophobic organic group, such as methyltriethoxysilane and the like, is used as a starting material of the matrix, is hydrolyzed and then neutralized, the polymer composition forms a deposit in an aqueous solution. As a result, it has been difficult to produce a microcapsule by incorporating a hydrophobic core material with the polymerization of a hydrolyzate of an alkoxysilane in the aqueous solution.

On the other hand, U.S. Pat. No. 3,551,346 teaches a method in which a polysiloxane is synthesized from a trialkoxysilane in the production of a microcapsule. However, the polysiloxane does not have sufficient strength as a capsule wall (as admitted by this U.S. patent). Therefore, this U.S. patent discloses a method for producing a microcapsule having a capsule wall of a two-layer structure by further making simultaneously a capsule wall by a conventional coacervation method. In addition, it is believed that any more than a certain amount a trialkoxysilane can not be used for producing a capsule wall since the trialkoxysilane is confined in an inner phase by the newly generated polysiloxane capsule wall. Therefore, this method is not admitted as a general method for producing a microcapsule composed only of the polysiloxane capsule wall.

Further, JP-B-60-25185, JP-B-3-10309, JP-B-5-70496, JP-B-7-62109, etc. disclose examples wherein a wall of a microcapsule is produced by cross-linking a polysiloxane having a functional group which can participate in cross-linking and polymerization. However, it is difficult to handle such a specific polysiloxane having a functional group participating in cross-linking and polymerization.

As described above, it has been difficult to easily produce a microcapsule having a capsule wall composed of organopolysiloxane according to conventional technologies.

It is advantageous also in cost to directly produce a microcapsule by making, from a hydroxysilane precursor having various properties, an organopolysiloxane capsule wall that can utilize such properties. Further, microcapsules suited for an object can be easily designed by combining various hydroxysilane precursors. For example, they can be expected to produce various capsule walls such as a capsule wall having tight compact network, a capsule wall having an appropriate permeation property, or a capsule wall having high strength or being suitably soft. However, it has been difficult to produce a microcapsule while controlling conditions such as polymerization rate, solubility and the like when solely using a hydroxysilane precursor having a low molecular weight.

SUMMARY OF THE INVENTION

An object of the present invention is to provide a microcapsule that contains a core material, wherein the microcapsule contains a capsule wall composed of organopolysiloxane having excellent properties. Another object of the present invention is to provide a method for producing such a microcapsule easily and with high productivity from generally available silicon compounds.

The present inventors have intensively studied a method for producing a microcapsule having a capsule wall composed of organopolysiloxane directly from a hydroxysilane precursor in order to solve the above-described problems. As a result, the inventors have found that the above-described object can be attained if:

one or more compounds (A) selected from the group of compounds represented by the following general formula (I) are hydrolyzed to produce one or more compounds (B) selected from the group of compounds represented by the following general formula (II):

$$R_nSiX_{(4-n)} \qquad \text{Formula (I)}$$

wherein, n represents an integer from 0 to 3; R represents an organic group in which a carbon atom is directly connected to a silicone atom, and when n is greater than 1, each of the R groups may be the same or different; and X represents at least one group selected from the group consisting of a hydroxyl group, hydrogen, alkoxy group, halogen group, carboxyl group, amino group and siloxy group, and when (4−n) is greater than 1, each of the groups X may be the same or different; and

$$R_nSi(OH)_mY_{(4-m-n)} \qquad \text{Formula (II)}$$

wherein, m represents an integer from 1 to 4; n represents an integer from 0 to 3; m+n≦4; R represents an organic group in which a carbon atom is directly connected to a silicone atom, and when n is greater than 1, each of the R groups may be the same or different; and Y represents at least one group selected from the group consisting of an alkoxy group, hydrogen and siloxy group, and when (4−m−n) is greater than 1, each of the groups Y may be the same or different; provided that the compound (B) comprises at least one compound of formula(II) wherein m=2 or 3 and at least one of R group possesses affinity for at least one of a continuous phase and a dispersed phase; and the compound (B) is polycondensed to synthesize organopolysiloxane constituting a capsule wall. The present invention was thus completed.

The term "continuous phase" and "dispersed phase" usually represent a dispersing medium and a dispersed phase before formation of a wall of a microcapsule respectively. In this specification, an outer phase and an inner phase after formation of a wall of a microcapsule are also called and referred to as "continuous phase" and "dispersed phase", respectively.

According to the present invention, organopolysiloxane constituting a wall of a microcapsule can be synthesized directly from the compound (B) belonging to the so-called hydroxysilanes. Further, the above-described organopolysiloxane can constitute a capsule wall necessary for producing a microcapsule containing core material, thus not requiring formation of a capsule wall by a conventional coacervation method.

The present invention provides a microcapsule containing core material and a capsule wall, in which the capsule wall of the microcapsule comprises:

organopolysiloxane synthesized by polycondensing a compound (B), monomer or monomeric mixture, wherein compound (B) contains one or more compounds represented by the general formula (II):

$$R_nSi(OH)_mY_{(4-m-n)} \quad (II)$$

wherein, m represents an integer from 1 to 4; n represents an integer from 0 to 3; m+n≦4; R represents an organic group in which a carbon atom is directly connected to a silicone atom, and when n is greater than 1, each of the R groups may be the same or different; and Y represents at least one group selected from the group consisting of an alkoxy group, hydrogen and siloxy group, and when (4−m−n) is greater than 1, each of the groups Y may be the same or different; provided that the compound (B) comprises at least one compound of formula(II) wherein m=2 or 3 and at least one of R group possesses affinity for at least one of a continuous phase and a dispersed phase.

The present invention further provides a method for producing a microcapsule containing core material which comprises a process wherein the compound (B) is polycondensed to synthesize organopolysiloxane and form the capsule wall.

The compound (B), which is used for producing a microcapsule having a core material encapsulated therein, as provided by the present invention, is usually obtained by hydrolyzing a compound (A), monomer or monomeric mixture, wherein compound (A) contains one or more compounds represented by the following general formula (I):

$$R_nSiX_{(4-n)} \quad (I)$$

wherein, n represents an integer from 0 to 3; R represents an organic group in which a carbon atom is directly connected to a silicone atom, and when n is greater than 1, each of the R groups may be the same or different; and X represents at least one group selected from the group consisting of a hydroxyl group, hydrogen, alkoxy group, halogen group, carboxyl group, amino group and siloxy group, and when (4−n) is greater than 1, each of the groups X may be the same or different; provided that the compound (A) contains at least one compound of formula (I) having an R group which possesses affinity for at least one of a continuous phase and a dispersed phase.

DETAILED DESCRIPTION OF THE PREFERRED EMBODIMENTS

In the present invention, the term "microcapsule" means a capsule such as a microcapsule, nanocapsule and the like, and thus has a broad meaning in comparison with the typical narrower meaning of the term "microcapsule". For example, in general, a "microcapsule" in a narrow sense means a capsule having a particle size of 1 μm to 1 mm and a "nanocapsule" means a capsule having a particle size less than 1 μm. As such, unless otherwise mentioned herein, the term "microcapsule" means a microcapsule in its broad sense in this specification and includes both microcapsules and nanocapsules. The phrase "microcapsule containing core material" means a microcapsule containing core material in the hollow space formed by a capsule wall.

The compound (B) is a compound or a group of two or more compounds selected from those represented by the general formula (II). At least one compound constituting the compound (B) is represented by the general formula (II) wherein m=2 or 3. At least one compound constituting the compound (B) is a compound having at least one R group which possess affinity for at least one of a continuous phase and a dispersed phase.

The capsule wall of the microcapsule containing core material of the present invention is formed by polycondensing the compound (B) to synthesize organopolysiloxane.

The condensation of the compound (B) is a reaction in which a —SiOH group in the general formula (II) is reacted with —SiL— (wherein, L represents a leaving group such as a hydroxyl group and the like) in aother molecule constituting the compound (B) or another prepolymer to form an —SiOSi— linkage. By this condensation reaction, organopolysiloxane is formed which constitutes a capsule wall.

As explained below, in the production of a microcapsule containing core material of the present invention, the condensation of the compound (B) is conducted to a certain extent to prepare a prepolymer of the compound (B) before the formation of organopolysiloxane, which constitutes a capsule wall. Therefore, the prepolymer is also constituted by organopolysiloxane formed by the condensation reaction.

The formulation of the organopolysiloxane which is formed as described above and constitutes the capsule wall in the present invention or a prepolymer is represented by the following general formula:

$$(R_3SiO_{1/2})_h(R_2SiO)_i(RSiO_{3/2})_j(SiO_2)_k(R'O_{1/2})_p \quad (III)$$

wherein, R represents an organic group in which a carbon atom is directly connected with a silicon atom, or represents hydrogen and when two or more R groups are present, they may be the same or different; h, i, j, k represents 0 or a positive integer; R' represents an alkyl group or hydrogen; p represents 0 or a positive integer; and 0≦h+p≦j+2k+2.

As described above, if two or more R groups are connected to one silicon atom in the general formula (III), the R groups may be the same or different each other. The formulations shown in parentheses directly before subscripts h, i, j may all be the same or different. For example, the R groups in $(R_3SiO_{1/2})_h$ may all be the same or different.

Organopolysiloxane constituting a prepolymer grows to be a larger polymer constituting a capsule wall, by way of condensation reaction of SiOH on a prepolymer with SiL (wherein, L represents a leaving group such as a hydroxyl group and the like) on another prepolymer. Therefore, although both organopolysiloxane constituting a capsule wall and organopolysiloxane constituting a prepolymer are represented by the above-described general formula (III), the values of h, i, j, k and p in the general formula (III) are different in the prepolymer and the capsule wall. Namely, when the above-described general formula (III) represents organopolysiloxane constituting a capsule wall, at least one of i and j is such a positive integer that a polymer sufficient to form a microcapsule is obtained. When the above-described general formula (III) represents organopolysiloxane constituting prepolymer, h, i, j and k represent 0 or a positive integer that is smaller than the h, i, j and k when the above-described general formula (III) represents organopolysiloxane constituting a capsule wall. The value of p depends on the extent of hydrolysis of the compound (B) obtained by hydrolysis of the compound (A), and the extent of condensation reaction of the compound (B). It is in the range wherein organopolysiloxane constituting a prepolymer and a capsule wall is sufficiently formed.

In an organopolysiloxane synthesized by polycondensation of the compound (B), an alkoxy group, a hydroxyl group and the like may partially remain on a silicon atom, or none of them may remain at all.

The compound (B) used for producing the microcapsule of the present invention having a core material therein is obtained by hydrolysis of the compound (A). The compound (A) is a compound or a group of two or more compounds selected from the group of compounds represented by the general formula (I).

The method for producing the microcapsule containing core materials of the present invention include processes using the following steps in order:

"(1) Producing the compound (B) by hydrolysis of the compound (A)",
"(2) Polycondensating by neutralizing of the compound (B)
"(3) Mixing and emulsificating with a core material and/or a second liquid phase", and
"(4) Curing treatment".

Further to the above steps, an "Over coat treatment", mentioned below or a "Surface treatment by the compound (A)" (hereinafter, abbreviated as "Surface treatment") may also be carried out before the "Curing treatment" step, if necessary or desired.

Examples of the compound (A) used in the production method of the present invention include a compound or a group of compounds carrying a hydrophilic group, a compound or a group of compounds carrying a hydrophobic group, a compound or a group of compounds carrying a group having affinity with a fluorocarbon, tetraalkoxysilane, a compound or a group of compounds carrying an amphiphatic group, a compound or a group of compounds carrying a surface active group, and the like. The term "amphiphatic" as used herein referrs to means having affinity against both of two media, which can not mix with each other, and the amphiphatic group is a group carrying both groups having mutually different affinities such as a hydrophilic group and a hydrophobic group.

The compound (A) used in the production method of the present invention may be composed of one kind of compound and/or one kind of group of compounds or be composed of a combination of several kinds of compounds and/or several kinds of groups of compounds. For example, the compound (A) may be composed of a compound carrying a hydrophilic group and a compound carrying a hydrophobic group.

The kind of the compound (A), and the proportion of several kinds of compounds and/or several kinds of groups of compounds, when the compound (A) is composed of several kinds of compounds and/or several kinds of groups of compounds, is preferably selected so that a prepolymer formed by condensation of the compound (B) obtained by hydrolysis of the compound (A) possess affinity with at least one of a continuous phase and dispersed phase, and the prepolymer formed is dispersed steadily.

In a compound carrying a hydrophilic group which composes compound (A), it is preferable that the R group in the general formula (I) carries a hydrophilic group, and the R group carrying a hydrophilic group is connected to a silicon atom. Two or more R groups carrying a hydrophilic group maybe connected to one silicon atom. When a plurality of hydrophilic groups are connected to one R group, the plurality of hydrophilic groups may include two or more kinds of hydrophilic groups. In addition to a hydrophilic group, a hydrophobic group and a group having affinity with a fluorocarbon may be connected to R group carrying a hydrophilic group.

Examples of a compound which derives a hydrophilic group in the compound (A) include polyethers such as a polyoxyethylene, polyoxypropylene and polyoxyethylene-polyoxypropylene copolymer, saccharides including polysaccharides and monosaccharides such as pullulan, sorbitol, chitin and chitosan or amino sugars, proteins, antibodies, hydrolyzed protein, polyamino acids, carboxylic acids or salts and derivatives thereof, polycarboxylic acids or salts and derivatives thereof, sulfuric acid or salts and derivatives thereof, phosphoric acid or salts and derivatives thereof, sulfonic acid or salts and derivatives thereof, phosphonic acid or salts and derivatives thereof, quaternary ammonium groups, amine or salts thereof, polyamines or salt thereof, and the like. The compound which derives a hydrophilic group in the compound (A) is not limited to the above-exemplified compounds. As a group which is connected with the above-exemplified hydrophilic group to form hydrophilic group "R", —$CH_2$—, —$(CH_2)_2$—, —$(CH_2)_3$—, —$(CH_2)_3OCH_2CH(OH)CH_2$—, —$(CH_2)_3NHCO$—, —$(CH_2)_3CH(CH_2COOH)CO$—, —$(CH_2)_3CH(COOH)CH_2CO$— and the like are exemplified, and a silicon atom is connected to the left side of this partial structural formula and the above-described hydrophilic group is connected to the right side of the formula.

Specific examples of a compound carrying a hydrophilic group and composing the compound (A) include polyoxyethylene-modified silicones [for example, KF-354 (trade name)] carrying, as a hydrophilic group, a polyether such as a polyoxyethylene, polyoxypropylene and polyoxyethylene-polyoxypropylene copolymer, polyethoxypropyltrimethoxysilanes [for example, KBM-641 (trade name) manufactured by Shin-Etsu Chemical Co., Ltd.], N-[2-hydroxy-3-(3'-trihydroxysilyl)propoxy]propyl hydrolyzed protein derived from γ-glycidoxypropyltriethoxysilane and hydroxylzed protein, N-[2-hydroxy-3-(3'-dihydroxymethylsilyl)propoxy]propyl hydrolyzed protein derived from γ-glycidoxypropylmethyldiethoxysilane and hydroxylzed protein(JP-A-8-67608), and compounds derived from the hydrophilic substance carrying a hydrophilic group as described above and a silane coupling agent such as β-(3,4-epoxycyclohexyl)ethyltrimethoxysilane, γ-[N-(β-aminoethyl)amino]propylmethyldimethoxysilane, γ-[N-(β-aminoethyl)amino]propyltrimethoxysilane, γ-[N-(β-aminoethyl)amino]propyltriethoxysilane, γ-aminopropyltrimethoxysilane, γ-aminopropyltriethoxysilane, γ-(N-phenylamino) propyltrimethoxysilane, γ-chloropropyltrimethoxysilane, γ-mercaptopropyltrimethoxysilane, γ-isocyanate propyltriethoxysilane, 3-triethoxysilylpropylsuccinic anhydride and the like. The compound carrying a hydrophilic group and composing compound (A) is not limited to the above-described examples.

Regarding the above-described polyethers such as a polyoxyethylene, polyoxypropylene and polyoxyethylene-polyoxypropylene copolymer, it is preferable that the number-average polymerization degree of oxyethylene and oxypropylene is from 1 to 2000, particularly from 4 to 800.

Preferable examples of the hydrolyzed protein in the above-described N-[2-hydroxy-3-(3'-trihydroxysilyl) propoxy]propyl hydrolyzed protein and N-[2-hydroxy-3-(3'-dihydroxymethylsilyl)propoxy]propyl hydrolyzed protein include, but are not limited to, hydrolysates of animal-derived protein such as collagen, elastin, keratin, fibroin (silk), sericin (silk), casein and conchiolin, vegetable-derived protein such as wheat protein, soybean protein, sesame protein and zein (corn protein), and microorganism-derived protein such as yeast protein. It is preferable that the number-average molecular weight of the hydrolyzed protein is from about 100 to 50000, particularly from about 200 to 5000.

In a compound carrying a hydrophobic group which composes the compound (A), it is preferable that the R group in the general formula (I) carries a hydrophobic group and the R group carrying a hydrophobic group is connected to a silicon atom. Two or more R groups carrying a hydrophobic group may be connected to one silicon atom, and a plurality of hydrophobic groups are connected to one R group. The plurality of hydrophilic groups may include two or more kinds of hydrophobic groups. In addition to a hydrophobic group, a group having affinity with a fluorocarbon may be connected to an R group carrying a hydrophobic group.

Examples of the hydrophobic group include a straight-chain hydrocarbon, branched hydrocarbon, unsaturated hydrocarbon, aromatic compounds, esters and the like. It is preferable that one or more of these functional groups are connected to R, although the hydrophobic group is not limited to the above-exemplified compounds.

Specific examples of a compound carrying a hydrophobic group and composing the compound (A) include methyldiethoxysilane, methyldichlorosilane, methyltrimethoxysilane, methyltriethoxysilane, methyltrichlorosilane, dimethyldimethoxysilane, dimethyldiethoxysilane, dimethyldichlorosilane, phenyltrimethoxysilane, phenyltriethoxysilane, phenyltrichlorosilane, diphenyldimethoxysilane, diphenyldiethoxysilane, diphenyldichlorosilane, hexyltrimethoxysilane, octyltriethoxysilane, decyltrimethoxysilane, stearoxypropyltrimethoxysilane, vinyltrimethoxysilane, vinyltriethoxysilane, vinyltris-(β-methoxyethoxy)silane, vinyltrichlorosilane, γ-methacryloxypropylmethyldimethoxysilane, γ-methacryloxypropyltrimethoxysilane, γ-methacryloxypropylmethyldiethoxysilane, γ-methacryloxypropyltriethoxysilane, γ-chloropropyltrimethoxysilane, γ-mercaptopropyltrimethoxysilane, octadecyldimethyl-(3-trimethoxysilylproyl)ammonium chloride, dimethylhexadecyl-(3-trimethoxysilylpropyl)ammonium chloride and the like. The specific examples further include compounds derived from the hydrophobic substance carrying a hydrophobic group as described above and a silane coupling agent such as vinyltrimethoxysilane, vinyltriethoxysilane, vinyltris(β-methoxyethoxy)silane, vinyltrichlorosilane, γ-methacryloxypropylmethyldimethoxysilane, γ-methacryloxypropyltrimethoxysilane, γ-methacryloxypropylmethyldiethoxysilane, γ-methacryloxypropyltriethoxysilane, γ-glycidoxypropyltriethoxysilane, γ-glycidoxypropylmethyldiethoxysilane, β-(3,4-epoxycyclohexyl)ethyltrimethoxysilane, γ-[N-(β-aminoethyl)amino]propylmethyldimethoxysilane, γ-[N-(β-aminoethyl)amino]propyltrimethoxysilane, γ-[N-(β-aminoethyl)amino]propyltriethoxysilane, γ-aminopropyltrimethoxysilane, γ-aminopropyltriethoxysilane, γ-(N-phenylamino) propyltrimethoxysilane, γ-chloropropyltrimethoxysilane, γ-mercaptopropyltrimethoxysilane, γ-isocyanatepropyltriethoxysilane and 3-triethoxysilylpropylsuccinic anhydride. Further, as specific examples of the compound represented by the general formula (I) in which X is a siloxy group, octamethylcyclotetrasiloxane, dihydrogenehexamethylcyclotetrasiloxane and trihydrogenepentamethylcyclotetrasiloxane are listed. The compound carrying a hydrophobic group and composed of the compounds (A) is not limited to the above exemplified compounds.

In the compound carrying a group having affinity with a fluorocarbon, it is preferable that the R group in the general formula (I) carries a group having affinity with a fluorocarbon, and the R group carrying a group having affinity with a fluorocarbon is connected to one silicon atom. Two or more R groups carrying a group having affinity with a fluorocarbon may be connected to one silicon atom, and a plurality of groups having affinity with a fluorocarbon may be connected to the R group. The plurality of groups having affinity with a fluorocarbon may include two or more kinds of groups having affinity with a fluorocarbon.

Examples of the compound carrying a group having affinity with a fluorocarbon and composing the compounds (A) include $C_8F_{17}CH_2CH_2Si(OCH_3)_3$, $CF_3CH_2CH_2Si(OCH_3)_3$, and compounds derived from a substance having affinity with a fluorocarbon and a silane coupling agent such as vinyltrimethoxysilane, vinyltriethoxysilane, vinyltris(β-methoxyethoxy)silane, vinyltrichlorosilane, γ-methacryloxypropylmethyldimethoxysilane, γ-methacryloxypropyltrimethoxysilane, γ-methacryloxypropylmethyldiethoxysilane, γ-methacryloxypropyltriethoxysilane, γ-glycidoxypropyltriethcxysilane, γ-glycidoxypropylmethyldiethoxysilane, β-(3,4-epoxycyclohexyl)ethyltrimethoxysilane, γ-[N-(β-aminoethyl)amino]propylmethyldimethoxysilane, γ-[N-(β-aminoethyl)amino]propyltrimethoxysilane, γ-[N-(β-aminoethyl)amino]propyltriethoxysilane, γ-aminopropyltrimethoxysilane, γ-aminopropyltriethoxysilane, γ-(N-phenylamino) propyltrimethoxysilane, γ-chloropropyltrimethoxysilane, γ-mercaptopropyltrimethoxysilane, γ-isocyanatepropyltriethoxysilane and 3-triethoxysilylpropylsuccinic anhydride. The compound carrying a group having affinity with a fluorocarbon and composing the compound (A) is not is not limited to the above exemplified compounds.

As specific examples of the compound having both a hydrophilic group and a hydrophobic group, which composes the compound (A), a compound which generates N-[2-hydroxy-3-(3'-dihydroxymethylsilyl)propoxy]propyl hydrolyzed protein by hydrolyzing the substituents such as an alkoxy group and the like are exemplified.

When the microcapsule containing core material, made from the compound (A), is dispersed in water or hydrophilic continuous phase, the compound (A) is as follows.

When a hydrophilic group in the compound (A) is a polyether such as a polyoxyethylene, polyoxypropylene and polyoxyethylene-polyoxypropylene copolymer, it is preferable that total number-average polymerization degree of oxyethylene and oxypropylene is from 10 to 1000, particularly from about 20 to 400. When the compound (A) is a hydrolyzed protein, it is preferable that the number-average molecular weight thereof is from 200 to 50000, particularly from about 400 to 5000.

It is preferable that the molar ratio of a compound (A) carrying a hydrophilic group (including the case wherein the R group carries a hydrophilic group and a hydrophobic group together) to a compound (A) carrying a hydrophobic group is from about 1:0 to 1:1000, particularly from about 1:2 to 1:200, in terms of monomers.

When a monomethyl type compound, wherein only one R group in the formula (I) is a methyl group, is used as the compound (A) carrying a hydrophobic group, it is preferable that at least one compound selected from the group consisting of methyltriethoxysilane, methyltrimethoxysilane and methyltrichlorosilane is used, or that such a compound is used in combination with at least one compound selected from the group consisting of dimethyldiethoxysilane, dimethyldimethoxysilane, dimethyldichlorosilane, octamethylcyclotetrasiloxane, phenyltriethoxysilane, hexyltrimethoxysilane, octyltriethoxysilane, decyltrimethoxysilane and stearoxypropyltrimethoxysilane. The molar ratio of the monomethyl type compound to another compound carrying a hydrophobic group may be from 100:0 to 0:100, but it is preferable that the molar ratio is from about 100:3 to 100:80, in terms of monomers. The monomethyl type compound and the other compounds carrying a hydrophobic group are not limited to the above-exemplified compounds.

When the microcapsule containing core material is made from the compound (A), and is dispersed in a hydrophobic continuous phase or non-aqueous continuous phase, the compound (A) is as follows.

When a hydrophilic group in the compound (A) is a polyether such as a polyoxyethylene, polyoxypropylene and polyoxyethylene-polyoxypropylene copolymer, it is preferable that total number-average polymerization degree of oxyethylene and oxypropylene is from 3 to 20, particularly from 5 to 10. When the compound (A) is a hydrolyzed protein, it is preferable that the number-average molecular weight thereof is from about 100 to 2000, particularly from about 200 to 1000.

When a monomethyl type compound wherein only one R group in the formula (I) is a methyl group is used as the compound (A) carrying a hydrophobic group, it is preferable that at least one compound selected from the group consisting of methyltriethoxysilane, methyltrimethoxysilane and methyltrichlorosilane is used, or such a compound is used in combination with at least one compound selected from the group consisting of dimethyldiethoxysilane, dimethyldimethoxysilane, dimethyldichlorosilane, octamethylcyclotetrasiloxane, phenyltriethoxysilane, hexyltrimethoxysilane, octyltriethoxysilane, decyltrimethoxysilane and stearoxypropyltrimethoxysilane. The molar ratio of the monomethyl type compound to another compound carrying a hydrophobic group may be from 100:0 to 0:100, but it is preferable that the molar ratio is from about 10:100 to 80:100, in terms of monomers. The monomethyl type compound and the other compounds carrying a hydrophobic group are not limited to the above-exemplified compounds.

Hydrolysis of the compound (A) will be described below.

The compound (B) is usually obtained by hydrolysis of the compound (A). As a medium for this hydrolysis, water is usually used. In addition, a small amount of an organic solvent soluble in water, salts, protein modifying agent such as urea, and the like may also be added to water. Addition of these additives is effective when neutralization after hydrolysis of the compound (A) or emulsification by mixing with a second liquid phase are conducted at a temperature of not more than 0° C., and is one preferable method. Further, in a process from hydrolysis of the compound (A) to production of a prepolymer via the compound (B), it is preferable to use a medium having a viscosity of 10 to 2000 mPa·s before addition of the compound (A), to control reaction speed so that the condensation reaction rate does not rise so much, to prevent deposition following insolubilization of the prepolymer, and to stabilize the solution. As a thickening substance for preparing a medium having a viscosity of 10 to 2000 mPa·s, polyvinyl alcohol, polyacrylamide, carboxymethylcellulose sodium, carboxymethyldextran, hydroxyethylcellulose, carageenan, chitin, chitosan, polypeptide, gelatin, sericin and the like are exemplified. In particular, an aqueous gelatin solution having a viscosity of 10 to 2000 mPa·s is exemplified.

It is preferable that the hydrolysis of the compound (A) is conducted at a temperature from −5° C. to 90° C., particularly from 5° C. to 75° C., with complete stirring (i.e. under stirring conditions).

The hydrolysis of the compound (A) may be conducted at either an acidic pH or a basic pH. Selection of these properties depends on the nature of the compound (A).

When the hydrolysis of the compound (A) is conducted at an acidic pH, it is preferably conducted at pH 1–5, particularly of 2–4. When acidity in hydrolysis is too strong, a core material may not be later incorporated thereto sufficiently, and a hyaline substance may be partially produced, though it depends also on the constitution and concentration of the compound (A). Examples of the acid to be used include an organic acid such as acetic acid and the like, and an inorganic acid such as hydrochloric acid, sulfuric acid, phosphoric acid and the like. Particularly, when the compound (A) carries a hydrophilic group which is a hydrolyzate of an animal-derived protein such as collagen, elastin, keratin, fibroin (silk), sericin (silk), casein and conchiolin, if the hydrolysis of the compound (A) is conducted at an acidic pH, preferable results are obtained for obtaining a microcapsule containing core material.

When the hydrolysis is conducted at a basic pH, it is preferably conducted at a pH of 7.5 to 11.5, particularly of 8 to 10. When basicity in hydrolysis is too strong, a core material may not be later incorporated therein sufficiently, and a hyaline substance may be partially produced, though it depends also on the constitution and concentration of the compound (A). As the alkali to be used, for example, sodium hydroxide, potassium hydroxide and the like are listed. Particularly, when the compound (A) carries a hydrophilic group which is a hydrolyzate of vegetable-derived protein such as for example wheat protein, soybean protein and sesame protein, if the hydrolysis of the compound (A) is conducted at a basic pH, preferable results are obtained for obtaining a microcapsule containing core material.

The compound (B) produced by hydrolysis of the compound (A) is polycondensed usually by neutralization.

The neutralization is preferably conducted at a temperature from −30° C. to 80° C., particularly from −5° C. to 55° C. with sufficient stirring. As acids and akalis used for the neutralization, the same compounds as those listed for the above-described hydrolysis are exemplified. As the medium for the neutralization, water is exemplified.

In the production method of the present invention, production of the compound (B) and polycondensation by neutralization are conducted to a certain extent before mixing and emulsification with a core material and/or second liquid phase, in order to prepare a prepolymer of the compound (B) previously. When at least one compound (B) which carries at least one hydrophilic R, particularly, carries at least one polypeptide having a number-average molecular weight of about 100 to 50000, as R, or a polyoxyethylene having a number-average polymerization degree of 1 to 2000, as R, is used, this method is particularly preferable since the prepolymer can be stabilized in this method.

Extent of the polycondensation of the compound (B) by neutralization to be conducted before mixing and emulsification with a core material and/or second liquid phase may be changed according to the other conditions as long as the formed prepolymer is stable. In other words, mixing and emulsification with a core material and/or second liquid phase must be conducted before the formed prepolymer become unstable.

When the prepolymer is unstable and easily precipitated, a method for preparing a prepolymer by hydrolysis of the compound (A) in a viscous solution such as an aqueous gelatin solution and the like is preferable since the prepolymer can be stabilized in this method.

It is preferable that after preparation of the prepolymer, this prepolymer in an aqueous solvent is mixed with a hydrophobic substance and/or a non-aqueous solvent to prepare an emulsion.

In the above-described method, after mixing of a hydrophobic substance and/or a non-aqueous solvent, the prepolymer causes mutual condensation and grows to a larger polymer to become organopolysiloxane constituting a capsule wall.

Then, mixing and emulsification with a core material and/or second liquid phase is utilized as described below.

The following methods are exemplified methods for mixing and emulsification with a core material and/or second liquid phase:

In the case of a microcapsule containing core material dispersed in water or a hydrophilic dispersing medium, a method in which a prepolymer is prepared in an aqueous dispersing medium, then, a core material in the form of liquid (second liquid phase) alone, or a core material and a solvent thereof (second liquid phase), is added.

In the case of a microcapsule containing core material dispersed in a hydrophobic dispersing medium or a non-aqueous dispersing medium, when the core material is soluble in an aqueous solvent or is hydrophilic, a method in which, to an aqueous solvent dispersion of a prepolymer, the core material is added as it is, or after being dissolved in an aqueous solvent, and the resulted liquid is mixed with a solvent immiscible with the aqueous solvent (continuous phase in the second liquid phase) to invert the phase and emulsify. The core material may be added after the inversion of the phase and emulsification thereof.

In the method of the present invention, since a core material can be incorporated at neutral condition, a microcapsule containing a substance unstable at conditions other than neutral can be produced. Mixing and emulsification with a core material and/or second phase are usually conducted at from −30° C. to 95° C., particularly from −5° C. to 60° C. Examples of the core material utilized are provided below.

Examples of the core material utilized include water, fatty acids particularly higher fatty acid, hydrocarbons, organic solvents, esters, phenols, silicones, silanes, metal alkoxides, alcohols particularly higher alcohol, animal and vegetable oils, extracted components, electrodonative coloration organic compounds, coloring matters, ultraviolet ray absorbers, vitamins, effective drug components, aroma components, preservative, sterilizer, salts; amino acid and its derivatives, protein, hydrolyzed protein and its derivatives, saccharides, polysaccharide, enzymes, fluorocarbon-like substances, and the like. The core material is not limited to the above-exemplified substances.

Examples of the higher fatty acids include capric acid, lauric acid, miristic acid, palmitic acid, stearic acid, behenic acid, 12-hydroxystearic acid, undecylenic acid, lanolin fatty acid, isostearic acid, linoleic acid, oleic acid, linolenic acid, arachidonic acid, eicosapentaenoic acid, docosahexaenic acid and the like.

Examples of the hydrocarbons include liquid paraffin, isoparaffin, ozokerite, pristan, ceresin, vaseline, microcrystalline wax and the like.

Examples of the organic solvent include hexane, heptane, octane, benzene, toluene, xylene, chlorobenzene, ethyl acetate, butyl acetate and the like.

Examples of the esters include isopropyl miristate, cetyl octanoate, octyldodecyl miristate, isopropyl palmitate, butyl stearate, hexyl laurate, miristyl miristate, decyl oleate, hexyldecyl dimethyloctanoate, cetyl lactate, miristyl lactate, lanolin lactate, methyl isostearate, isocetyl stearate, cholesteryl 12-hydroxystearate, ethylene glycol di-2-ethylhexylate, dipentaerythrithol fatty ester, n-alkyl glycol monoisostearate, propylene glycol dicaprate, neopentyl glycol dicaprate, glyceryl tricaprate, isostearyl neopentanoate, diisostearyl malate, glyceryl monostearate, glyceryl distearate, glyceryl di-2-heptylundecanoate, trimethylolpropane tri-2-ethylhexanoate, trimethylolpropane triisostearate, neopentyl glycol di-2-ethylhexanoate, pentaerythritol tetra-2-ethylhexanoate, glyceryl tri-2-ethylhexanoate, cetyl 2-ethylhexanoate, 2-ethylhexyl isononanoate, isononyl isononanoate, isodecyl isononanoate, isotridecyl isononanoate, 2-ethylhexyl palmitate, glyceryl trimiristate, glyceryl trioctanoate, glyceryl triisopalmitate, castor oil fatty acid methyl ester, oleyl oleate, glyceryl acetate, 2-heptylundecyl palmitate, diisopropyl adipate, diisobutyl adipate, N-lauroyl-L-glutamic acid-2-octyldodecyl ester, 2-heptylundecyl adipate, ethyl laurate, di-2-ethylhexyl sebacate, 2-hexyldecyl miristate, 2-hexyldecyl palmitate, 2-hexyldecyl adipate, 2-hexyldecyl succinate, diisopropyl sebacate and the like.

Examples of the phenols include t-butylphenol, nonylphenol, dodecylphenol, α-naphthol, β-naphthol, hydroquinone monomethyl ether, p-chlorophenol, p-bromophenol, o-phenylphenol, p-phenylphenol, methyl p-hydroxybenzoate, ethyl p-hydroxybenzoate, propyl p-hydroxybenzoate, 3-isopropylcatechol, p-t-butylcatechol, 4,4'-methylenediphenol, bisphenol A, 1,2-dihydroxynaphthalene, chlorocatechol, bromocatechol, 2,4-dihydroxybenzophenone, phenolphthalein, methyl gallate, ethyl gallate, propyl gallate, hexyl gallate, octyl gallate, dodecyl gallate, cetyl gallate, stearyl gallate, tannic acid, phenol resin, zinc salicylate, zinc t-butylsalicylate and the like.

Examples of the silicones include dimethylpolysiloxane, methylphenylpolysiloxane, dimethylsiloxanemethylstearoxysiloxane copolymer, dimethylsiloxane-methylmethoxysiloxane copolymer, dimethylsiloxane-methylethoxysiloxane copolymer, trimethylsiloxysilicic acid, methylcyclopolysioxane, methylhydrogenpolysiloxane, high polymer methylpolysiloxane, crosslinked-type methylpolysiloxane and the like.

Examples of the silanes include methyltrimethoxysilane, methyltriethoxysilane, phenyltrimethoxysilane, phenyltriethoxysilane, hexyltrimethoxysilane, octyltrimethoxysilane, decyltrimethoxysilane, tetramethoxysilane, tetraethoxysilane and the like.

Examples of the metal alkoxides include trimethyl borate, triethyl borate, tetraethyl titanate, tetraisopropyl titanate and the like.

Examples of the higher alcohols include capryl alcohol, lauryl alcohol, miristyl alcohol, cetyl alcohol, stearyl alcohol, arachyl alcohol, behenyl alcohol, oleyl alcohol, ketostearyl alcohol, monostearyl glyceryl ether, 2-decyltetradecanol, 2-hexyldecanol, 2-hexyldodecanol, 2-octyldodecanol, 2-heptylundecanol, lanolin alcohol, cholesterol, phytosterol, isostearyl alcohol and the like.

Examples of the animal and vegetable oils include avocado oil, tsubaki oil, macadamia nut oil, corn oil, olive oil, evening primrose oil, rapeseed oil, yolk oil, sesame oil, persic oil, wheat germ oil, camellia sasanqua oil, castor oil, curing castor oil, linseed oil, safflower oil, cotton seed oil, curing cotton seed oil, soybean oil, curing soybean oil, peanut oil, tee nip oil, Japanese Nutmeg oil, rice bran oil, chinese tung oil, japanese tung oil, cinnamon oil, jojoba oil, germ oil, almond oil, cocoa oil, palm oil, curing palm oil, horse tallow, turtle oil, mink oil, squalane, squalene, orange roughy oil, beef tallow, curing beef oil, beef bone oil, neat's foot oil, mutton oil, lard, train oil, curing train oil, fish oil, curing fish oil, lanolin, lanolin alcohol, hydrogenater lanolin, lanolin acetate, liquid lanolin, lanolin fatty acid isopropyl ester, cholesteryl lanonate, cyclic lanolin, polyoxyethylenelanolin alcohol ether, polyoxyethylenelanolin alcohol acetate, polyethylene glycol lanolin fatty acid, polyoxyethylene hydrogenater lanolin alcohol ether, carnauba wax, candelilla wax, jojoba wax, hard lanolin, Japan wax, indian millet wax, cotton wax, wax myrtle, insect wax, montan wax, rice bean wax, shellac wax, jojoba wax, bee wax, train wax, jojoba alcohol, abietic acid, hydrogenated abietic acid and the like.

Examples of the electrodonative coloration organic compound include diarylphthalides, polyaryl carbinols, leuco auramines, acyl auramines, aryl auramines, rhodamine-β-lactams, indolines, spiropyrans, fluorans and the like. Specific examples thereof include crystal violet lactone, malachite green lactone, Michler's hydrol, cryltal violet carbinol, malachite green carbinol, N-(2,3-dichlorophenyl)leuco auramine, N-benzoyl auramine, N-acetyl auramine, N-phenyl auramine, rhodamine-β-lactam, 2-(phenyliminoethanedilidene)-3,3-dimethylindoline, N-3, 3-trimethylindolinobenzspirolane, 3-dietylamino-6-methyl-7-chlorofluoran, 3-diethylamino-7-methoxyfluoran, 3-diethylamino-6-benzyloxyfluoran, 1,2-benz-6-diethylaminofluoran and the like.

Examples of the coloring matters include colorless white pigments such as titanium dioxide, zinc oxide and the like, inorganic red pigments such as iron oxide (red iron oxide), iron titanate and the like, inorganic brown pigments such as γ-iron oxide and the like, inorganic yellow pigments such as yellow iron oxide, loess and the like, inorganic black pigments such as black iron oxide, carbon black, lower titanium oxide and the like, inorganic violet pigments such as mango violet, cobalt violet and the like, inorganic green pigments such as chromium oxide, chromium hydroxide, cobalt titanate and the like, inorganic blue pigments such as ultramarine, iron blue and the like, organic dyes such as Red 201, Red 202, Red 204, Red 205, Red 218, Red 220, Red 225, Red 226, Red 228, Red 405, Orange 201, Orange 203, Orange 204, Yellow 401, Green 202, Blue 404 and the like, organic pigments of zirconium, barium or aluminum lake and the like such as Red 3, Red 104, Red 106, Red 227, Red 230, Red 401, Red 505, Orange 205, Yellow 4, Yellow 5, Yellow 202, Yellow 203, Green 3, Violet 201, Blue 11 and the like, natural pigments such as chlorophyll, β-carotene and the like, mica titanium, red iron oxide-treated mica titanium, yellow iron oxide-treated mica titanium, black iron oxide-treated mica titanium, iron oxide- yellow iron oxide-treated mica titanium, ultramarine-treated mica titanium, carmine-treated mica titanium, chromium oxide-treated mica titanium, carbon black-treated mica titanium and the like. Further, examples thereof include talc, kaolin, mica, phlogopite, sericite, white mica, synthetic mica, epidolite, lithia mica, vermiculite, inorganic powders such as apatite fluoride, hydroxyapatite, ceramic powder, metal soap (zinc miristate, calcium palmitate, aluminum stearate and the like), boron nitride, silica-alumina, silica-magnesia, bentonite, fuller's earth, Japanese acid clay, active white earth, montmorillonite, attapulgite and the like; and organic powder such as a polyamide resin powder (nylon powder), polyethylene powder, polymethyl methacrylate powder, polystyrene powder, styrene-acrylic acid copolymer resin powder, benzoguanamine resin powder, polyethylene tetrafluoride powder, cellulose powder; and the like.

Examples of the ultraviolet ray absorbers include salicylic acid-based ultraviolet ray absorbers such as phenyl salicylate, p-t-butylphenyl salicylate, p-octylphenyl salicylate and the like, benzophenone-based ultraviolet ray absorbers or derivatives thereof such as 2,4-dihydroxybenzophenone, 2-hydroxy-4-methoxybenzophenone, 2-hydroxy-4-octyloxybenzophenone, 2-hydroxy-4-dodecyloxybenzophenone, 2,2'-dihydroxy-4,4'-dimethoxybenzophenone, 2,2'-dihydroxy-4-methoxybenzophenone, 2-hydroxy-4-methoxy-5-sulfobenzophenone and the like, 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3', 5'-di-t-amylphenyl)benzotriazole, 2-[2'-hydroxy-3'-(3",4", 5",6"-tetrahydrophthalimidemethyl)-5'-methylphenyl]-benzotriazole, 2-(2'-hydroxyl-3'-dodecyl-5'-methylphenyl) benzotriazole, 2-(2'-hydroxy-3'-undecyl-5'-methylphenyl) benzotriazole, 2-(2'-hydroxy-3'-tridecyl-5'-methylphenyl) benzotriazole, 2-[2'-hydroxy-4'-(2"-ethylhexyl)oxyphenyl] benzotriazole, 2-[2'-hydroxy-4'-(2"-ethyloctyl)oxyphenyl] benzotriazole, 2-[2'-hydroxy-4'-(2"-propyloctyl)oxyphenyl] benzotriazole, 2-[2'-hydroxy-4'-(2"-propylheptyl) oxyphenyl]benzotriazole, 2-[2'-hydroxy-4'-(2"-propylhexyl) oxyphenyl]benzotriazole, 2-[2'-hydroxy-4'-(1"-ethylhexyl) oxyphenyl]benzotriazole, 2-[2'-hydroxy-4'-(1"-ethylheptyl) oxyphenyl]benzotriazole, 2-[2'-hydroxy-4'-(1"-ethyloctyl) oxyphenyl]benzotriazole, 2-[2'-hydroxy-4'-(1"-propyloctyl) oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, condensate of methyl-3-[3-t-butyl-5-(2H-benzotriazole-2-yl)-4-hydroxyphenyl]propionate with polyethylene glycol (molecular weight:about 300), derivatives or ester of p-methoxycinnamic acid such as 2-ethylhexyl p-methoxycinnamate, derivatives or ester of p-dimethylaminobenzoic acid such as 2-ethylhexyl p-dimethylaminobenzoate, derivatives or ester of cinnamic acid such as benzyl cinnamate, derivatives of anthranylate, salicylate and benzooxazole, 2,4,6-tri-(p-anilino)-1-(carboxy-2'-ethylhexyl)-1,3,5-triazine, derivatives of dibenzoylmethane such as 4-t-butyl-4'-methoxydibenzoylmethane and 4-isopropyldibenzoylmethane, franone derivatives, ferulic acid or esters thereof, γ-oryzanol and the like.

Examples of the vitamins include vitamins or derivatives thereof such as vitamin A, vitamin B, vitamin C, vitamin D, vitamin E, thiamine hydrochloride, pyridoxine hydrochloride, calcium panthothenate, bisbentiamine, methylmethioninesulfonium chloride and the like. Specifically, magnesium L-ascorbyl-2-phosphate, sodium L-ascorbyl-2-phosphate, tocopherol acetate and the like are exemplified.

Examples of the effective drug components include sulfur drugs such as sulfamethomidine, circulatory drugs such as calcium hobatate, papaverine hydrochloride, diltiazem hydrochloride and reserpine, breathing promoting drugs such as trimetoxynol hydrochloride, bromhexine hydrochloride and tipepidine hibenzate, antitussive expectoration drugs, antibiotics such as potassium benzylpenicillinate, sodium benzylpenicillinate, potassium phenoxymethylpenicillinate and ampicillin, carcinostatic tumor agents such as 5-fluorourasil, N-(2-tetrahydrofuryl)-5-fluorourasil and bleomycin hydrochloride, treating agent such as timepidium bromide, lidocaine hydrochloride and chlorpromazine hydrochloride, antihistamic agents such as diphenhydramine hydrochloride and chlorphenylamine maleate, antiphlogistic agent such as aspirin, quinine hydrochloride and sulpirin, bactericides such as salicylic acid, hinoki cypress, sulfur, parabenes and the like, preservatives, and in addition, photosensitive materials, cyctein or derivatives thereof, guaiazlene or derivatives thereof, glutathione or derivatives thereof, and the like.

Examples of the extracted components include oil-soluble arnica extract, aloe extract, oil-soluble dead nettle extract, matricaria extract, oil-soluble chamomile extract, oil-soluble glycyrrhiza extract, cape jasmine extract, oil-soluble mulberry extract, oil-soluble burdock extract, oil-soluble collagen extract, oil-soluble salvia extract, oil-soluble lithospermum root extract, oil-soluble linden extract, oil-soluble betula alba extract, oil-soluble field horsetail extract, oil-soluble yarrow extract, oil-soluble sage extract, Japanese green gentian extract, common thyme extract, citrus unshiu peel extract, oil-soluble juglanus regia L. extract, oil-soluble Japanese angelica root extract, oil-soluble common marigold extract, oil-soluble carrot extract, oil-soluble wild rose extract, oil-soluble loquat leaf extract, oil-soluble placental extract, oil-soluble hop extract, oil-soluble marronnier extract, oil-soluble peach leaf extract, mugwort extract, oil-soluble coix extract, lavender extract, lemon extract, orange extract, oil-soluble rosemary extract, oil-soluble royal jelly extract, green tea, Du Zhong tea or Ruibosu tea which contain tannins or flavonoids; and crude drugs of plant and animal origin or various salts thereof such as sophora japonica, scutellaria root and Souhakuhi extract.

Examples of the aroma components include oils having odor such as almond, anise, caraway, cassia, cedar leaf, cedar wood, cinnamon, citronella, clove, eucalyptus, geranium, grape fruit, lavender, lemon, lemon herb, rose oil, lime, orange flower (nerori oil), nutmeg, onion, garlic, orange, lignum vitae, orris, peppermint, pine, pine needle, rosemary, sandalwood, sassafras, spearmint, time, coffee, black tea, cherry, apple, pineapple, banana, peach, vanilla and the like.

Examples of the salts include calcium carbonate, magnesium carbonate, magnesium silicate, calcium silicate, aluminum silicate, barium silicate, barium sulfate, strontium silicate, metal tungstate, silica, zeolite, barium sulfate, calcined calcium sulfate (baked gypsum), calcium phosphate, lithium chloride, sodium chloride, potassium chloride, ammonium chloride, lithium bromide, sodium bromide, potassium bromide, lithium iodide, sodium iodide, potassium iodide, iodine, sodium sulfate, potassium sulfate, ammoniumsulfate, ammonium nitrate, lime nitrogen, lime perphosphate, baked phosphatic fertilizer, sodium phosphate and the like.

Examples of the amino acid, protein, saccharides and the like include amino acids or peptides such as potassium aspartate, magnesium aspartate, sodium glutamate, lysine hydrochloride and glutathione, animal-derived proteins such as collagen, elastin, keratin, fibroin, sericin, casein and conchiolin, vegetable-derived proteins such as wheat protein, soybean protein and sesame protein, microorganism-derived proteins such as yeast protein or hydrolysates of such proteins, placenta extract, mucopolysaccharides, urea and the like.

Examples of the enzyme include lipase, protease, super oxide, dismutase, lysozyme, alkaliphosphatase, amylase, pancreatin, glutathione peroxidase, catalase and the like.

Examples of the fluorocarbon-like substance include Fomblin HC/04 (trade name), Fomblin HC/25 (trade name) and Fomblin HC/R (trade name) which are a liquidperfluoro ether which is a kind of polyoxy perfluofoalkanes manufactured by Monteflous (Milan, Italy).

One or more of the above-described compounds can be used as core materials. However, the core material is not limited to the above-exemplified compounds.

As a material of the continuous phase, a material which is liquid during the capsule preparation process is used. In the case of a microcapsule containing core material dispersed in a hydrophobic continuous phase or non-aqueous continuous phase, examples of materials of the continuous phase include higher fatty acids, hydrocarbons, organic solvents, esters, silicones, higher alcohols, animal and vegetable oils and the like, which are exemplified as the core materials. One or more materials among them are used for the materials of the continuous phase. Among organic solvents, even a material having a boiling point lower than that of water may also be used providing it can expel water from the system azeotropically.

In preparation of emulsion, when a particle is prepared of which particle size is essentially from 0.3 to 100 μm and the median particle size is in the range from 1 to 20 μm in a 2-liter round bottom cylindrical glass reaction vessel having an internal diameter of 12 cm equipped with a mechanical stirrer, it is preferable that the reaction solution is stirred at a speed from 50 to 1000 rpm, particularly from 300 to 1000 rpm.

In preparation of emulsion, when a reaction solution is stirred by a mechanical stirrer and then a particle is prepared, of which the particle size is essentially from 0.1 to 30 μm and the median particle size is from 0.5 to 5 μm by a homomixer, it is preferable that the reaction solution is treated by the homomixer at a speed of from 1000 to 20000 rpm, particularly from 5000 to 10000 rpm.

In preparation of emulsion, when a reaction solution is stirred by a mechanical stirrer, treated by a homomixer and then a particle is prepared, of which the particle size is essentially from about 0.1 to 1 μm and the median particle size is from about 0.2 to 0.8 μm by a microfluidizer, it is also preferable that the reaction solution is treated by the microfluidizer at a speed of from about 300 to 5000 kg/cm$^2$.

One object of the treatment by a homomixer and microfluidizer is to decrease the particle size. Another object is to produce a microcapsule containing core material wherein the capsule wall is not decomposed when shearing strength generated in this treatment is applied.

The treatment by a homomixer or a microfluidizer may be repeated two times or more to decrease the particle size more. When ultraviolet ray absorber is used as a core material, repeating the treatment by a homomixer or a microfluidizer often has another effect which decreases the amount of free ultraviolet ray absorber in the dispersion.

The preparation of emulsion in the presence of alcohol, particularly polyhydric alcohol such as ethylene glycol, polyethylene glycol, glycerin or the like, may be conducted in order to decrease the particle size more. When ultraviolet ray absorber is used as a core material, this method often has another effect which decreases the amount of free ultraviolet ray absorber in the dispersion.

The preparation of emulsion in ultrasonic wave may also be conducted in order to decrease the particle size more.

Next, surface treatment of a microcapsule containing core material by the compound (A) during production will be described below.

A microcapsule containing core material can be produced even if the surface treatment by the compound (A) during production of a microcapsule containing core material is not conducted. However, according to the production method of the present invention, it is guessed that a silanol group which did not participate in condensation remains on the surface of an uncured capsule immediately after emulsification. Therefore, a surface treatment with the compound (A) is preferably conducted to prevent coagulation of a microcapsule containing core material.

When the compound (A) for surface treatment is a compound which is easily hydrolyzed in water such as a chlorosilane including trimethylchlorosilane and hexamethylsilazane, it is preferable that this compound (A) is added to the emulsion solution after emulsification and then, the solution is neutralized.

When the compound (A) for surface treatment is an alkoxysilane like trimethlethoxysilane, it is necessary that following emulsification, this neutral solution is made somewhat acidic or basic and the alkoxysilane is hydrolyzed once. Also when a compound (A) carrying a silanol group from the beginning is used as it is for surface treatment, it is necessary that following emulsification, this neutral solution is made somewhat acidic or basic. Then, the compound (A) is fixed on the surface of a capsule by neutralization. The control of pH should be conducted carefully so that the capsule is not decomposed. In the case of treatment at an acidic pH, the pH is preferably from about 3 to 6.5. In the case of treatment at a basic pH, the pH is preferably from about 7.5 to 10. Examples of the compound (A) used in this surface treatment will be described below, however, it is not limited to the exemplified compounds.

One object of the surface treatment is to prevent coagulation of a microcapsule containing core material. It is preferable to add, after preparation of emulsion, a compound (A) carrying 3 alkyl groups on a silicon atom such as trimethylchlorosilane, ethoxytrimethylsilane, t-butyldimethylchlorosilane, hexamethyldisiloxane, hexamethyldisilazane and the like, to prevent coagulation of a microcapsule containing core material.

Further, after preparation of emulsion, a compound (A) carrying a cationic group as an organic substituent such as octadecyldimethyl-(3-trimethoxysilylpropyl)ammonium chloride can be added, hydrolyzed and neutralized to make the surface of a microcapsule containing core material cationic.

Further, it is possible, after preparation of emulsion, to variously modify the properties of the surface of a microcapsule containing core material and to obtain various functions by controlling pH to neutralize a compound (A) such as methyldiethoxysilane, methyldichlorosilane, tetramethoxysilane, tetraethoxysilane, tetrachlorosilane, methyltrimethoxysilane, methyltriethoxysilane, methyltrichlorosilane, dimethyldimethoxysilane, dimethyldiethoxysilane, dimethyldichlorosilane, octamethylcyclotetrasiloxane, phenyltrimethoxysilane, phenyltriethoxysilane, phenyltrichlorosilane, diphenyldimethoxysilane, diphenyldiethoxysilane, diphenyldichlorosilane, hexyltrimethoxysilane, octyltriethoxysilane, decyltrimethoxysilane, stearoxypropyltrimethoxysilane, vinyltrimethoxysilane, vinyltriethoxysilane, vinyltris-(β-methoxyethoxy) silanevinyltrichlorosilane,
γ-methacryloxypropylmethyldimethoxysilane,
γ-methacryloxypropyltrimethoxysilane,
γ-methacryloxypropylmethyldiethoxysilane,
γ-methacryloxypropyltriethoxysilane,
γ-chloropropyltrimethoxysilane,
γ-mercaptopropyltrimethoxysilane,
γ-isocyanatepropyltriethoxysilane,
3-triethoxysilylpropylsuccinic anhydride, octadecyldimethyl-(3-trimethoxysilylpropyl)ammonium chloride, dimethylhexadecyl-(3-trimethoxysilylpropyl) ammonium chloride, methoxy(ethoxy)$_n$(propoxy)$_m$propylmethyldialkoxysilane, methoxy(ethoxy)$_n$(propoxy)$_m$propyltrialkoxysilane, a compound (A) derived from γ-glycidoxypropyltriethoxysilane,
γ-glycidoxypropylmethyldiethoxysilane and another substance, such as N-[2-hydroxy-3-(3'-trihydroxysilyl) propoxy]propyl hydrolyzed protein and N-[2-hydroxy-3-(3'-dihydroxymethylsilyl)propoxy]propyl hydrolyzed protein, a compound (A) derived from a silane coupling agent such as β-(3,4-epoxycyclohexyl)ethyltrimethoxysilane, γ-[N-(β-aminoethyl)amino]propylmethyldimethoxysilane, γ-[N-(β-aminoethyl)amino]propyltrimethoxysilane, γ-[N-(β-aminoethyl)amino]propyltriethoxysilane,
γ-aminopropyltrimethoxysilane,
γ-aminopropyltriethoxysilane, γ-(N-phenylamino) propyltrimethoxysilane, vinyltrimethoxysilane, vinyltriethoxysilane, vinyltris-(β-methoxyethoxy) silanevinyltrichlotosilane,
γ-methacryloxypropylmethyldimethoxysilane,
γ-methacryloxypropyltrimethoxysilane,
γ-methacryloxypropylmethyldiethoxysilene,
γ-methacryloxypropyltriethoxysilane,
γ-chloropropyltrimethoxysilane,
γ-mercaptopropyltrimethoxysilene,
γ-isocyanatepropyltriethoxysilane,
3-triethoxysilylpropylsuccinic anhydride and other substance.

The above-described series of surface treatments may be combined.

In the curing treatment of the instant invention, the strength of a wall of a microcapsule containing core material can be increased by further progressing the polycondensation reaction by removal of alcohol generated in hydrolysis of an alkoxysilane, which is a kind of the compound (A), or by dehydration due to the lapse of time or by heating and removal of water out of the reaction system, and the like. The temperature of the reaction solution is preferably 30° C. or more. Heating at the boiling point of water in the reaction system is particularly preferable, although the boiling point may be changed by control of pressure. The above-described dehydration due to the lapse of time occurs since the siloxane condensation naturally progresses at neutral pH. The removal of water out of the system means for example distilling off (condensed water obtained by cooling of solvent vapor is removed out of the reaction system without returning it to the reaction system) and the like.

In thus obtained microcapsule containing core material, it is preferable that the weight of the core material is from about 0.01 to 99% by weight based on the weight of the microcapsule containing core material. This ratio of the weight of the core material to the weight of the microcapsule containing core material is hereinafter referred to "core weight ratio". According to the present invention, a wide range of the core weight ratio can be obtained, the thickness of the capsule wall is easily controlled by correlating the core weight ratio with the particle size.

The microcapsule containing core material has sufficient water resistance when it is used at a pH around neutral.

The strength of the capsule depends on the kind of the compound (A) used, particle size, curing conditions, and core weight ratio. As an example, in the case of a microcapsule produced for cosmetics having a particle size of 1 to 2 μm and a core weight ratio of 90%, even if it was compounded in a cosmetic via mechanical mixing process and applied on skin, no decomposition was recognized.

The microcapsule containing core material produced according to the present invention can be treated by freeze-drying and spray-drying to be made into a powder.

The intake ratio of a core material into a microcapsule containing core material produced according to the present invention is from about 50 to 99.9% on a weight to weight basis, and in preferable cases, from about 80 to 98% on a weight to weight basis. This intake ratio shows how much % of a core material is incorporated in the capsule.

Though the microcapsule produced according to the above-explained method exerts an excellent effect, incorporation of a core material into the capsule is not necessarily complete. A part of the core material may remain in the continuous phase, and may continuously leak out of the capsule into continuous phase with the lapse of time.

When a part of the core material remains in the continuous phase, and continuously leaks out of the capsule into the continuous phase with the lapse of time, various undesirable problems may occur.

For example, an object of preventing contact of the core material with skin, which is suggested in cosmetic fields and the like, can not be attained when the core material remains in the continuous phase or leaks into the continuous phase. Further, although it is suggested that an unstable material which is unstable and discolors with the lapse of time when exposed to outer atmosphere is incorporated into a microcapsule for insulation from the atmosphere and prevention of discoloring with the lapse of time, the object of the invention can not fully be accomplished if incorporation of the core material into the capsule is not complete.

In addition to the object mentioned above, there is another object of the present invention, which is to provide a microcapsule having a capsule wall made of a specific organopolysiloxane and a method for producing the same in which the amount of a core material that has not been incorporated into a capsule is minimum, and leaking of the core material out of the capsule in later use is minimum.

That is, the present invention provides a microcapsule containing core material wherein the capsule wall is made of organopolysiloxane synthesized by polycondensation of a compound (B), wherein at least one compound selected from the group consisting of hydrolyzable silanes and hydrolyzable polysiloxanes is added to the core material.

The present invention further provides a microcapsule containing core material wherein the capsule wall is made of organopolysiloxane synthesized by polycondensation of a compound (B), and the surface of the formed capsule wall is treated at least once with a hydrolysate of at least one compound selected from the group consisting of hydrolyzable silanes and hydrolyzable polysiloxanes.

The present invention further provides a method for producing a microcapsule containing core material, comprising a step wherein at least one compound selected from the group consisting of hydrolyzable silanes and hydrolyzable polysiloxanes is added to a core material, and a step wherein a compound (B) is polycondensed to synthesize organopolysiloxane to form a capsule wall.

The present invention further provides a method for producing a microcapsule containing core material, comprising a step wherein a compound (B) is polycondensed to synthesize organopolysiloxane to form a capsule wall, and a step wherein the surface of the formed capsule wall is treated at least once with a hydrolysate of at least one compound selected from the group consisting of hydrolyzable silanes and hydrolyzable polysiloxanes.

In the microcapsule containing core material of the present invention, at least one compound selected from the group consisting of hydrolyzable silanes and hydrolyzable polysiloxanes is added to a core material, or the surface of the formed capsule wall is treated at least once with a hydrolysate of at least one compound selected from the group consisting of hydrolyzable silanes and hydrolyzable polysiloxanes, so that the amount of the core material which has not been incorporated into the capsule is minimum, or leaking out of the core material of the capsule in later use is minimum.

Herein, the term "hydrolyzable silanes" and "hydrolyzable polysiloxanes" respectively mean silanes and polysiloxanes which generate a silanol group by being hydrolyzed. As the hydrolyzable silanes and hydrolyzable polysiloxanes to be added to a core material or to be used for the treatment of the surface of the formed capsule wall, methyltrichlorosilane, methyldichlorosilane, dimetyldichlorosilane, trimethylchlorosilane, phenyltrichlorosilane, diphenyldichlorosilane, methyltrimethoxysilane, methyltriethoxysilane, phenyltrimethoxysilane, phenyltriethoxysilane, diphenyldimethoxysilane, diphenyldiethoxysilane, hexyltrimethoxysilane, octyltriethoxysilane, decyltrimethoxysilane, tetramethoxysilane, tetraethoxysilane and $Me_3SiO(Me_2SiO)_f[MeZSio]_gSiMe_3$(f represents an integer from 5 to 50, and g represents an integer from 2 to 100 and Z represents hydrogen or an alkoxy group) are exemplified. Particularly preferable examples thereof include tetramethoxysilane, tetraethoxysilane, methyltrichlorosilane, $Me_3SiO(Me_2SiO)_f[MeZSiO]_g SiMe_3$(f represents an integer from 5 to 50, and g represents an integer from 2 to 100, f/g=0.1 to 20, weight-average molecular weight (M.W.)=200 to 10000, and Z represents hydrogen, a methoxy group or ethoxy group) and the like.

At least one compound selected from the group consisting of hydrolyzable silanes and hydrolyzable polysiloxanes is usually added to a core material previously, and added to the continuous phase together with the core material.

The treatment of the surface of the formed capsule wall with a hydrolysate of at least one compound selected from the group consisting of hydrolyzable silanes and hydrolyzable polysiloxanes (hereinafter, referred to as over coat treatment) is conducted at least once. It is conducted after mixing and emulsification, and usually before surface treatment of the capsule wall with a compound (A) and the like, namely, prevention of coagulation and curing treatment of the capsule wall. This over coat treatment is usually conducted by adding to the continuous phase at least one compound selected from the group consisting of hydrolyzable silanes and hydrolyzable polysiloxanes. The over coat treatment is preferably conducted with stirring at approximately the same temperature as that in the mixing and emulsification. The amount added of at least one compound selected from the group consisting of hydrolyzable silanes and hydrolyzable polysiloxanes is from 0.1 to 30 mol, preferably from 0.5 to 10 mol per 100 of the total mol number of Si used for formation of the capsule wall.

If the intake ratio is not sufficiently high, purification such as removal of a core material which has not been incorporated in, and the like is usually required. Examples of the purification methods are as follows.

One purification method is that in which a liquid phase not dispersing the capsule and unmixable with the other liquid phase dispersing a capsule is added, said two liquid phases are mixed completely, then both liquids are separated by decantation or by liquid separation, after separation of the two phases, to transfer impurities to other liquid phase. When both liquid phases are not easily separated, centrifugal separation may be adopted. Further, when both liquid phases are not easily separated, liquid which is miscible with the liquid phase dispersing a capsule may be further added to wash and separate the capsule.

Another purification method is that in which a microcapsule containing core material precipitated or floated by centrifugal separation is collected portion-wise. In this case, after the above-described procedure, impurities are removed together with a solvent. The collected microcapsule is re-dispersed into a solvent which can disperse the capsule. This procedure is repeated.

There is a method by ultrafiltration as another purification method. In this purification method by ultrafiltration, impurities eluted by ultrafiltration are removed, and the concentrated microcapsule is re-dispersed into a solvent which can disperse a microcapsule containing core material. This procedure is repeated.

The microcapsule containing core material of the present invention is bio-inactive, and the capsule wall thereof has thermal and mechanical stability and light resistance which are general basic properties of an organopolysiloxane. The present invention is advantageous also in the point of cost since a microcapsule containing core material can be produced directly from a compound (A) such as analkoxysilane, halogenated silane, hydrogensilane, polysiloxane and the like. In addition, a wide range of microcapsules containing a core material can be easily designed according to various objects by combining various compounds (A).

The microcapsule containing core material of the present invention having such various properties can be widely applied to pharmaceuticals, liquid crystal, chemical products, recording materials, cosmetics, aromatics, enzymes, agriculture, adhesives, fiber, foods, catalysts, detergents, coloring matters, paints, preservatives, solvents and the like.

For example, when a microcapsule containing core material of the present invention using a ultraviolet ray absorber as the core material is applied to cosmetics, the following merits are obtained as compared with the case in which a ultraviolet ray absorber itself is compounded in cosmetics.

1. Safety of cosmetics increases since permeation of a ultraviolet ray absorber into skin decreases.
2. A more stable formulation becomes possible in formulation systems in which stable formulations are conventionally difficult.
3. When a ultraviolet ray absorber itself is compounded in cosmetics, addition of a stabilizer may be required for preventing yellowing of the ultraviolet ray absorber. However, there is no necessity of a stabilizer in this invention.
4. When an ultraviolet ray absorber such as ethylhexylmethoxycinnamic acid or the like is compounded itself, tackiness and the like occur, and when an ultraviolet ray absorber such as methoxybutylbenzoylmethane or the like is compounded itself, a crystal is deposited to cause roughness. However, in this invention, these problems are solved, and the use feeling of the cosmetics is increased. Further, the adhesion of the cosmetics also increases.
5. When an ultraviolet ray absorber itself is compound in a formulation having high water content such as a lotion and the like, it is necessary to add a certain amount of a surfactant. However, according to the present invention, there is no need of addition of a surfactant or only a small amount of a surfactant should be added, therefore, a ultraviolet ray absorber can be easily compounded. Further, methoxybutylbenzoylmethane or the like can not be easily compounded since it manifests poor solubility and the degree of solubility thereof decreases by the influence of other compounding components. In the present invention, however, compounding thereof is easy. Namely, according to the present invention, compatibility with other compounding components (raw material of cosmetics, oil, solvent and the like) increases.
6. Ultraviolet ray absorbing effect (SPF value), namely effect for protecting humane body from a ultraviolet ray, increases.

When a microcapsule containing an ultraviolet ray absorber as the core material is applied to cosmetics, the particle size of the microcapsule is preferably from 0.05 $\mu$m to 50 $\mu$m, more preferably from 0.3 $\mu$m to 30 $\mu$m, and the compounding amount (by weight) of the ultraviolet ray absorber is preferably from 0.1% to 50%, more preferably from 0.5% to 30%, based on the amount of the microcapsule.

When the microcapsule containing core material of the present invention is used for pharmaceuticals, cosmetics, coloring matters and the like, following ingredients, for example, are cooperatively used with the microcapsule:

fatty acids particularly higher fatty acid, hydrocarbons, organic solvents, esters, phenols, silicones, silanes, metal alkoxides, alcohols particularly higher alcohol, animal and vegetable oils, extracted components, electrodonative coloration organic compounds, coloring matters, ultraviolet ray absorbers, vitamins, effective drug components, aroma components, preservative, sterilizer, salts; amino acid and its derivatives, protein, hydrolyzed protein and its derivatives, saccharides, polysaccharide, enzymes, fluorocarbon-like substances, and the like, which are exemplified as the core material in the above paragraphs; and surfactants classified into anionic, cationic, nonionic, and amphoteric surfactants and the like which includes betaine type surfactant fatty acid salt, fatty acid hydrolyzed protein condensate, sulfate type surfactant, phosphate type surfactant, polyester and its derivatives.

EXAMPLE

Objects, characteristics and merits of the present invention are apparent from the following descriptions referring to various examples of the present invention, however, these descriptions are only illustrative and are not intended to restrict the scope of the present invention. All % and part in the following Examples are by weight unless otherwise stated.

Analysis Method 1

About 10 g of the dispersion of a microcapsule containing core material is weighed correctly, the water content of the dispersion of the microcapsule containing core material is measured with an infrared moisture meter LIBROR EB-280MOC (trade name) manufactured by Shimadzu Corp. From this result, the weight of the non-water portion in the dispersion containing a microcapsule [microcapsule containing core material+free core material (core material which has not been incorporated into a capsule)+ash] is calculated. In the case of an oil-in-water type capsule, the weight of the dispersion containing a capsule is the weight of [water+microcapsule containing core material+free core material+ash]. When the water content is measured according to this Analysis method 1, the weight of the non-water portion in the dispersion [microcapsule containing core material+free core material+ash] is calculated from the measured results.

Analysis Method 2

The concentration of Na in a capsule dispersion is measured by an ICP emission spectral analysis device SPS1700HVR (trade name) manufactured by Seiko Denshi Kogyo Ltd., and the weight of NaCl in the dispersion containing a microcapsule is calculated. As described in the above-described Analysis 1, it is believed that the dispersion containing a microcapsule contains also ash, and almost all portions other than silica in the ash are occupied by NaCl. Therefore, the amount of NaCl is measured by this Analysis method 2, and the result is used as an ash amount in calculating the core weight ratio, as described later.

Analysis 3

About 1 g of dispersion of a microcapsule containing core material is weighed correctly, and then is transferred into a 500 ml separating funnel while being washed with about 100 ml of water. 100 ml of n-hexane is added and the mixture is sufficiently shaken, then, allowed to stand still. After separation of liquid phase, 100 ml of the n-hexane-washed solution is transferred to another vessel. This separation operation is repeated three times, the resulting n-hexane-extracted solutions are combined, and concentrated correctly to 100 ml. 1 $\mu$l of this n-hexane extracted solution is drawn into a microsyringe, and subjected to liquid chromatography. The weight of free core material which has not been incorporated into the microcapsule, existing in about 1 g of the dispersion of the microcapsule containing core material, was measured based on a calibration curve of standard concentration separately made, and the weight of a free core material in the dispersion containing a microcapsule is calculated.

Analysis 4

About 0.1 g of the resulting dispersion of a microcapsule containing core material is weighed correctly, and to this is added 5 ml of a 5N sodium hydroxide aqueous solution and the mixture is stirred for one hour at 50° C. and cooled to room temperature. This is transferred into a 500 ml separating funnel while being washed with about 100 ml of water. 100 ml of n-hexane is added and the mixture is sufficiently shaken, then, allowed to stand still. After separation of the liquid phase, 100 ml of the n-hexane-washed solution is transferred to another vessel. This separation operation is repeated three times, the resulting n-hexane-extracted solutions are combined, and concentrated correctly to 100 ml. 1 $\mu$l of this n-hexane solution is drawn into a microsyringe, and subjected to liquid chromatography. The total weight of a free core material which has not been incorporated into the microcapsule and a core material which has been incorporated into the microcapsule existing in about 0.1 g of the resulting dispersion of the microcapsule containing core material was determined based on a calibration curve of a standard concentration that was separately made.

Core weight ratio, in terms of % by weight of the amount of a core material incorporated into a microcapsule based on the weight of the microcapsule is obtained by the following formula:

[(value by Analysis method 4)−(value by Analysis method 3)]/
[(value by Analysis method 1)−(value by Analysis method 2)−(value by Analysis method 3)]×100

Analysis Method 5

About 0.1 g of the resulting dispersion of a microcapsule containing core material is weighed, and about 5 ml of water is added to this. One drop of this is placed on a glass plate and covered by a cover glass, then, observed by an optical microscope at a magnification of 1000, and particle size distribution is visually measured.

Analysis Method 6

The particle size distribution of the resulting microcapsule containing core material is measured by SALD-2000 (trade name) manufactured by Shimadzu Corp.

Test Method 1

One drop (about 50 $\mu$l) of a dispersion of a microcapsule containing core material diluted by 20-fold is sandwiched between 2 pieces of glass plates that are 1 cm square and have a thickness of 2 mm, and this is placed on a horizontal hard base plate and a pressure of 1.5 kg/cm$^2$ is applied from the upper side. After application of the pressure, it is observed if the microcapsule is broken or not.

Example 1

Production of a microcapsule containing 2-ethylhexyl p-methoxycinnamate and having a capsule wall made of organopolysiloxane composed of a co-polycondensate of the hydrolysate of methoxy (ethoxy) n-propyldihydroxymethylsilane, methyltriethoxysilane and phenyltriethoxysilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 90 g of water, 10 g of a polyoxyethylene-modified silicone (KF-354A (trade name) manufactured by Shin-Etsu Silicone Co., Ltd., and produced by substituting both ends of methoxy (ethoxy) n-propyldihydroxymethylsilane with tri-methyl silyl groups.) and 0.2 g of 18% hydrochloric acid. A mixture of 4.4 g of methyltriethoxysilane and 1.2 g of phenyltriethoxysilane was added dropwise from the dropping funnel at 50° C. with stirring. The mixture was further stirred for 6 hours at 50° C., then, 1.6 g of 4% aqueous sodium hydroxide solution was aded dropwise with stirring to control the pH to 7.0. Thereafter, the mixture was stirred for 1 hour at 50° C.

2) Addition of Core Material and Emulsification 5.4 g of 2-ethylhexyl p-methoxycinnamate was added to the reaction solution prepared in the process 1) with stirring at 600 rpm, and the mixture was further stirred for 4 hours at 600 rpm.

3) Prevention of Coagulation and Curing Treatment of Capsule Wall 0.5 g of trimethylchlorosilane was added to the solution prepared in the process 2) in a reaction vessel with stirring at 600 rpm and 50° C., then, immediately, 1 g of a 20% aqueous sodium hydroxide solution was added dropwise. The temperature of the reaction solution was raised gradually to reflux. A vapor containing alcohol was distilled off, and the remaining mixture was further heated to reflux with stirring at 150 rpm for 6 hours. This reaction solution was cooled with stirring at 150 rpm at room temperature to obtain a microcapsule containing a core material.

Comparative Example 1

Polymerization is conducted at an interface between a continuous phase and a core material in the production of microcapsule containing 2-ethylhexyl p-methoxycinnamate and having a capsule wass made of organopolysiloxane composed of a co-polycondensate of the hydrolysate of methoxy (ethoxy) n-propyldihydroxymethylsilane, methyltriethoxysilane and phenyltriexhosysilane.

1) Preparation of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 90 g of water, 10 g of a polyoxyethylene-modified silicone (KF-354A (trade name) manufactured by Shin-Etsu Silicone Co., Ltd.) and 0.2 g of 18% hydrochloric acid. Thereto, a mixture of 4.4 g of methyltriethoxysilane and 1.2 g of phenyltriethoxysilane was added dropwise from the dropping funnel at 50° C. with stirring. The mixture was further stirred for 6 hours at 50° C., then, 5.4 g of 2-ethylhexyl p-methoxycinnamate was added with stirring of the reaction solution at 600 rpm. Further, the mixture was stirred for 4 hours at 600 rpm, then, 1.9 g of a 4% aqueous sodium hydroxide solution was added dropwise with stirring, to control the pH to 7.0. Thereafter, the mixture was stirred for 1 hour at 50° C.

2) Prevention of Coagulation and Curing Treatment of Capsule Wall 3 g of trimethylchlorosilane was added to the solution prepared in the process 1) with stirring at 600 rpm and 50° C. in the reaction vessel, then, 5.6 g of a 5N aqueous sodium hydroxide solution was added dropwise immediately. The temperature of the reaction solution was raised gradually to reflux. A vapor containing alcohol was distilled off, and the remaining mixture was further heated to reflux with stirring at 150 rpm for 6 hours. This reaction solution was cooled with stirring at 150 rpm at room temperature to obtain a product. An adhesive substance adhered to the wall of the reaction vessel, and only oil was separated in the about same amount with that of 2-ethylhexyl p-methoxycinnamate added.

Example 1A

Production of a microcapsule containing 2-ethylhexyl p-methoxycinnamate and having a capsule wall made of organopolysiloxane composed of a co-polycondensate of the hydrolysate of methoxy(ethoxy)n-propyldihydroxymethylsilane, methyltriethoxysilane and phenyltriexhosysilane.

A microcapsule containing core material was produced in the same manner as in Examples 1 except that 10 g of a polyoxyethylene-modified silicone was replaced with 3 g of polyethoxypropyltrimethoxysilane (KBM-641 manufactured by Shin-Etsu Silicone Co., Ltd.), the amounts of 4% aqueous sodium hydroxide solution, 2-ethylhexyl p-methoxycinnamate, trimethylchlorosilane and 20% aqueous sodium hydroxide solution were changed to 97 g, 4.2 g, 1.7 g, 4.0 g, 1.0 g and 1.8 g respectively, and the temperature at stirring after the pH was controlled to 7.0 was changed to 20° C.

The dispersion of the resulting microcapsule containing core material was analyzed according to Analysis methods 1 and 5 giving the following results.

| | |
|---|---|
| Water dispersion of a capsule having a diameter from 0.3 to 10 µm, mainly from 1 to 2 µm | 107 g |
| Components excepting water | 14.0% |

In Example 1, a microcapsule containing core material was produced by using polyether-modified silicone, KF-354A (trade name), as a compound (A) carrying a hydrophilic group, hydrolyzing this to prepare a prepolymer, adding a core material and conducting emulsification. However, when a polymer was produced at the interface between the core material and the continuous phase as in Comparative Example 1, a microcapsule containing core material was not formed, and the polymer was separated from the core material. In Example 1A, though a trialkoxysilane carrying a polyether group, KBK-641 (trade name), was used as a compound (A) carrying a hydrophilic group, a microcapsule containing core material could be produced like in Example 1.

The microcapsule containing core material that was obtained in Example 1A was tested to see if the capsule thereof was broken in the above-described Test method 1 or not. No breakage of the capsule was found.

Example 2

Production of a microcapsule containing 2-ethylhexyl p-methoxycinnamate and having a capsule wall made of organopolysiloxane composed of a co-polycondensate of the hydrolysate of N-[2-hydroxy-3-(3'-trihydroxysilyl)propoxy] propyl hydrolyzed collagen, methyltriethoxysilane and phenyltriethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 135 g of water, 15 g of N-[2-hydroxy-3-(3'-trihydroxysilyl)propoxy]propyl hydrolyzed collagen (number-average molecular weight of the hydrolyzed collagen is about 2000) and 3.6 g of 18% hydrochloric acid. Thereto, a mixture of 45.9 g of methyltriethoxysilane and 12.4 g of phenyltriethoxysilane was added dropwise from the dropping funnel at 50° C. with stirring.

The mixture was further stirred for 6 hours at 50° C. Then, 2.9 g of a 25% aqueous sodium hydroxide solution was added dropwise with stirring to control the pH to 7.0, and the mixture was further stirred for 1 hour at 50° C.

2) Addition of Core Material and Emulsification 389 g of 2-ethylhexyl p-methoxycinnamate was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Prevention of Coagulation and Curing Treatment of Capsule Wall 3.0 g of trimethylchlorosilane was added to the solution prepared in the process 3) in the original reaction vessel with stirring at 600 rpm and 50° C., then, 4.4 g of a 25% aqueous sodium hydroxide solution was added dropwise immediately. The temperature of the reaction solution was raised gradually to reflux. A vapor containing alcohol was distilled off, and the remaining mixture was further heated to reflux with stirring at 150 rpm for 2 hours. This reaction solution was cooled with stirring at 150 rpm at room temperature to obtain a microcapsule containing core material.

The dispersion of the resulting microcapsule containing core material was analyzed according to Analysis methods 1–5 giving the following results.

| | |
|---|---|
| Water dispersion of a capsule having a diameter from 0.3 to 5 μm, mainly from 1 to 2 μm | 850 g |
| Components excepting water | 50% |

The amount of free 2-ethylhexyl p-methoxycinnamate in the dispersion was 4%.

The amount of 2-ethylhexyl p-methoxycinnamate contained in the capsule was 84%.

Then, the free 2-ethylhexyl p-methoxycinnamate in the dispersion was removed by washing with hexane, and a microcapsule containing 2-ethylhexyl p-methoxycinnamate was obtained in purified condition. When the addition of methyltrichlorosilane and the following series of neutralization treatments were deleted in the prevention of coagulation and curing treatment of a capsule wall in the process 4), no difference from the present examples was recognized with the naked eyes, however, microscope observation revealed mutual adhesion of the microcapsule and partial coagulation. In the present examples, such coagulation was not recognized.

The microcapsule containing core material obtained in Example 2 was tested if the capsule thereof was broken in the above-described Test method 1 or not. No breakage of the capsule was found.

Example 2A

Production of a microcapsule containing a mixture of 2-ethylhexyl p-methoxycinnamate and 4-t-butyl-4'-methoxydibenzoylmethane and having a capsule wall made of organopolysiloxane composed of a co-polycondensate of the hydrolysate of N-[2-hydroxy-3-(3'-trihydroxysilyl)propoxy]propyl hydrolyzed collagen, methyltriethoxysilane and phenyltriethoxysilane.

A microcapsule containing core material was produced in the same manner as in Example 2 except that 389 g of 2-ethylhexyl p-methoxycinnamate was replaced with a mixture obtained previously by dissolving 19.5 g of 4-t-butyl-4'-methoxydibenzoylmethane in 78.2 g of 2-ethylhexyl p-methoxycinnamate and the dropwise addition of 2.9 g of a 25% aqueous sodium hydroxide solution and the following stirring were conducted at 20° C.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 315 g |
| Components excepting water | 42.3% |

As described above, in this Example 2A, 4-t-butyl-4'-methoxydibenzoylmethane as second core material could be simultaneously incorporated in a microcapsule in addition to 2-ethylhexyl p-methoxycinnamate.

The microcapsule containing core material obtained in Example 2A was tested if the capsule thereof was broken in the above-described Test method 1 or not. No breakage of the capsule was found.

Example 2B

Production of a microcapsule containing 2-ethylhexyl p-methoxycinnamate and having a capsule wall made of organopolysiloxane composed of a co-polycondensate of the hydrolysate of N-[2-hydroxy-3-(3'-trihydroxysilyl)propoxy]propyl hydrolyzed wheat protein, methyltriethoxysilane and phenyltriethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 283 g of water, 16.8 g of N-[2-hydroxy-3-(3'-trihydroxysilyl)propoxy]propyl hydrolyzed wheat protein (number-average molecular weight of the hydrolyzed wheat protein is about 400) and 4.5 g of a 20% aqueous sodium hydroxide solution. Thereto, a mixture of 24 g of methyltriethoxysilane and 3.2 g of phenyltriethoxysilane was added dropwise from the dropping funnel at 50° C. with stirring.

The mixture was further stirred for 6 hours at 50° C. Then, 4.1 g of a 18% hydrochloric acid was added dropwise with stirring to control the pH to 7.0, and the mixture was further stirred for 1 hour at 50° C.

2) Addition of Core Material and Emulsification 12.3 g of 2-ethylhexyl p-methoxycinnamate was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Prevention of Coagulation and Curing Treatment of Capsule Wall 1.2 g of trimethylchlorosilane was added to the solution prepared in the process 3) in the original reaction vessel with stirring at 600 rpm and 50° C., then, 1.4 g of a 20% aqueous sodium hydroxide solution was added dropwise immediately to control the pH at 5.5. The temperature of the reaction solution was raised gradually to reflux. A vapor containing alcohol was distilled off, and the remaining mixture was further heated to reflux with stirring at 150 rpm for 2 hours. This reaction solution was cooled with stirring at 150 rpm at room temperature to obtain a microcapsule containing core material.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 595 g |
| Components excepting water | 11% |

As described above, in this Example 2B, a microcapsule containing core material was produced using a compound (A) carrying a hydrophilic group composed of hydrolyzed wheat protein. The hydrolysis of the compound (A) was conducted under basic conditions.

Comparative Example 2

The same procedure and ingredients usued in Example 2B were utilized except that the hydrolysis of the silane was conducted at an acidic pH instead of hydrolysis at basic pH as occured in Example 2B. A large amount of adhesive materials adhered to the inner wall of the reaction vessel, and production of a microcapsule could not continue.

Example 2C

Production of a microcapsule containing 2-ethylhexyl p-methoxycinnamate and having a capsule wall made of organopolysiloxane composed of a co-polycondensate of the hydrolysate of N-[2-hydroxy-3-(3'-trihydroxysilyl)propoxy] propyl hydrolyzed soybean protein, methyltriethoxysilane and phenyltriethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 177 g of water, 9.3 g of N-[2-hydroxy-3-(3'-trihydroxysilyl)propoxy]propyl hydrolyzed soybean protein (number-average molecular weight of the hydrolyzed soybean protein is about 350) and 3.5 g of a 20% aqueous sodium hydroxide solution. Thereto, a mixture of 10 g of methyltriethoxysilane and 2.7 g of phenyltriethoxysilane was added dropwise from the dropping funnel at 50° C. with stirring.

The mixture was further stirred for 6 hours at 50° C. Then, 3.2 g of a 18% hydrochloric acid was added dropwise with stirring to control the pH to 7.0, and the mixture was further stirred for 1 hour at 50° C.

2) Addition of Core Material and Emulsification 6.5 g of 2-ethylhexyl p-methoxycinnamate was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Prevention of Coagulation and Curing Treatment of Capsule Wall 2.4 g of trimethylchlorosilane was added to the solution prepared in the process 3) in the original reaction vessel with stirring at 600 rpm and 50° C., then, 1.2 g of a 20% aqueous sodium hydroxide solution was added dropwise to control the pH to 5.5. The temperature of the reaction solution was raised gradually to reflux. A vapor containing alcohol was distilled off, and the remaining mixture was further heated to reflux with stirring at 150 rpm for 6 hours. This reaction solution was cooled with stirring at 150 rpm at room temperature to obtain a microcapsule containing core material.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 360 g |
| Components excepting water | 7.6% |

As described above, in this Example 2C, a microcapsule containing core material was produced using a compound (A) carrying a hydrophilic group composed of hydrolyzed soybean protein. The hydrolysis of the compound (A) was conducted under basic conditions.

The microcapsule containing core material obtained in Example 2C was tested if the capsule thereof was broken in the above-described Test method 1 or not. No breakage of the capsule was found.

Example 2D

A microcapsule containing core material was produced in the same manner as in Examples 2 except that 8.7 g of hexyltrimethoxysilane (KBM-3063 manufactured by Shin-Etsu Silicone Co., Ltd.) was used instead of the phenyltriethoxysilane, the amounts of methyltriethoxysilane and 2-ethylhexyl p-methoxycinnamate were changed to 38.3 g and 87.4 g respectively, and treatment with methyltrichlorosilane was not conducted.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 507 g |
| Components excepting water | 23.6% |

The microcapsule containing core material obtained in Example 2D was tested if the capsule thereof was broken in the above-described Test method 1 or not. No breakage of the capsule was found.

Example 2E

A microcapsule containing core material was produced in the same manner as in Examples 2 except that 6.7 g of decyltrimethoxysilane (KBM-3103C manufactured by Shin-Etsu Silicone Co., Ltd.) was used instead of the phenyltriethoxysilane, the amounts of methyltriethoxysilane and 2-ethylhexyl p-methoxycinnamate were changed to 30.0 g and 6.7 g respectively, and treatment with methyltrichlorosilane was not conducted.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 300 g |
| Components excepting water | 11.9% |

In these Example 2D and 2E, a microcapsule containing core material was produced even if a hydroxysilane having a hydrophobic group different to that used in Example 2 was used.

The microcapsule containing core material obtained in Example 2E was tested if the capsule thereof was broken in the above-described Test method 1 or not. No breakage of the capsule was found.

Example 2F

A microcapsule containing core material was produced in the same manner as in Examples 2 except that 15 g of N-[2-hydroxy-3-(3'-dihydroxymethylsilyl)propoxy]propyl hydrolyzed collagen having a number average molecular weight at peptide portion of about 2000 was used instead of N-[2-hydroxy-3-(3'-trihydroxysilyl)propoxy]propyl hydrolyzed collagen.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 687 g |
| Components excepting water | 54.3% |

As described above, in this Example 2F, a microcapusule containing a core material was produced even if N-[2-hydroxy-3-(3'-dihydroxymethylsilyl)propoxy]propyl hydrolyzed collagen was used instead of N-[2-hydroxy-3-(3'-trihydroxysilyl)propoxy]propyl hydrolyzed collagen.

The microcapsule containing core material obtained in Example 2A was tested if the capsule thereof was broken in the above-described Test method 1 or not. No breakage of the capsule was found.

Example 2G

A microcapsule containing core material was produced in the same manner as in Examples 2 except that 15 g of N-[2-hydroxy-3-(3'-dihydroxymethylsilyl)propoxy]propyl hydrolyzed collagen was used instead of N-[2-hydroxy-3-(3'-trihydroxysilyl)propoxy]propyl hydrolyzed collagen, 22.8 g of steayloxypropyltrimethoxysilane(KBM-6000 manufactured by Shin-Etsu Silicone Co., Ltd.) was used instead of phenyltriethoxysilane and the amount of 2-ethylhexyl p-methoxycinnamate was changed to 60 g.

The dispersion of the resulting microcapsule containing core material was analyzed according to Analysis methods 1–5 giving the following results.

| | |
|---|---|
| Water dispersion of a capsule having a diameter from 0.3 to 5 μm, mainly from 1 to 2 μm | 400 g |
| Components excepting water | 25% |

The amount of free 2-ethylhexyl p-methoxycinnamate in the dispersion was 6%.

The amount of 2-ethylhexyl p-methoxycinnamate contained in the capsule was 40%.

As described above, in this Example 2G, a microcapusule containing a core material was produced even if a hydroxysilane having a hydrophobic group different to that of the above mentioned Example 2F.

The microcapsule containing core material obtained in Example 2G was tested if the capsule thereof was broken in the above-described Test method 1 or not. No breakage of the capsule was found.

Example 2H

A microcapsule containing core material was produced in the same manner as in Examples 2 except that 45.9 g of methyltriethoxysilane was replaced with 19.1 g of dimethyldiethoxysilane and 23.0 g of methyltriethoxysilane and the amount of 2-ethylhexyl p-methoxycinnamate was changed to 97.7 g.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 460 g |
| Components excepting water | 27.1% |

As described above, in this Example 2H, a microcapusule containing a core material was obtained even if a part of trihydroxysilane was replaced with a dihydroxysilane.

The microcapsule containing core material obtained in Example 2H was tested if the capsule thereof was broken in the above-described Test method 1 or not. No breakage of the capsule was found.

Example 2I

A microcapsule containing core material was produced in the same manner as in Examples 2H except that 9.6 g of octamethylcyclotetrasiloxane was used instead of dimethyldiethoxysilane.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 425 g |
| Components excepting water | 25.1% |

As described above, in this Example 2I, a microcapusule containing a core material was obtained even if alkoxysilane used in Example 2H was replaced with a cyclosiloxane.

The microcapsule containing core material obtained in Example 2I was tested if the capsule thereof was broken in the above-described Test method 1 or not. No breakage of the capsule was found.

Example 2J

A microcapsule containing core material was produced in the same manner as in Examples 2F except that 16.2 g of isopropyl stearate and 4.1 g of abietic acid was used instead of 2-ethylhexyl p-methoxycinnamate and homomixer treatment was not conducted.

The dispersion of the resulting microcapsule containing core material was analyzed according to Analysis methods 1 and 5 giving the following results.

| | |
|---|---|
| Water dispersion of a capsule having a diameter from 1 to 100 μm, mainly from 10 to 50 μm | 226 g |
| Components excepting water | 30% |

As described above, in this Example 2J, a microcapusule containing abietic acid which is a solid resin at a room temperature was obtained by dissolving the abietic acid in isopropyl stearate.

The microcapsule containing core material obtained in Example 2J was tested if the capsule thereof was broken according to the above-described Test method 1 or not, to find that a capsule having a particle size of about 8 μm or more was broken. Particularly, in the condition wherein capsules having a particle size from 8 to 15 μm were broken, leaking of the core material out of the capsule was observed, and it was observed that the capsule wall and the core material are rounded respectively to form the shape of an "eight". However very little breakage was observed of a capsule having a particle size of less than 8 μm.

Example 2K

A microcapsule containing core material was produced in the same manner as in Examples 2F except that 15 g of N-[2-hydroxy-3-(3'-dihydroxymethylsilyl)propoxy]propyl hydrolyzed silk protein (fibroin) having a number average molecular weight at peptide portion of about 1000 was used instead of N-[2-hydroxy-3-(3'-dihydroxymethylsilyl) propoxy]propyl hydrolyzed collagen.

The dispersion of the resulting microcapsule containing core material was analyzed according to Analysis methods 1 and 5 giving the following results.

| | |
|---|---|
| Water dispersion of a capsule having a diameter from 1 to 100 μm, mainly from 10 to 50 μm | 375 g |
| Components excepting water | 20% |

As described above, in this Example 2K, a microcapusule containing core material was obtained even if the compound (A) having hydrolyzed silk protein (fibroin), as a hydrophilic group, was used.

The microcapsule containing core material obtained in Example 2K was tested if the capsule thereof was broken according to the above-described Test method 1 or not, to find that a capsule having a particle size of about 8 μm or more was broken. Particularly, in the condition wherein capsules having a particle size from 8 to 15 μm were broken, leaking of the core material out of the capsule was observed, and it was observed that the capsule wall and the core material are rounded respectively to form the shape of an "eight". However very little breakage was observed of a capsule having a particle size of less than 8 μm.

Example 2L

A microcapsule containing core material was produced in the same manner as in Examples 2F except that 10.5 g of castor oil was used instead of 2-ethylhexyl p-methoxycinnamate, and the amounts of methyltriethoxysilane and phenyltriethoxysilane were changed to 38.2 g and 10.3 g, respectively.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 300 g |
| Components excepting water | 15% |

As described above, in this Example 2L, a microcapusule containing castor oil which is a viscous liquid at a room temperature was obtained.

The microcapsule containing core material obtained in Example 2L was tested if the capsule thereof was broken in the above-described Test method 1 or not. No breakage of the capsule was found.

Example 2M

A microcapsule containing core material was produced in the same manner as in Examples 2 except that the amounts of methyltriethoxysilane and phenyltriethoxysilane were changed to 17.0 g and 4.6 g, respectively, 0.5 g of octadecyldimethyl-(3-trimethoxysilylpropyl)ammonium chloride was added simultaneously in adding them and 16.7 g of N-[2-hydroxy-3-(3'-dihydroxymethylsilyl)propoxy] propyl hydrolyzed collagen having a number average molecular weight at peptide portion of about 2000 was used instead of N-[2-hydroxy-3-(3'-trihydroxysilyl)propoxy] propyl hydrolyzed collagen.

The dispersion of the resulting microcapsule containing core material was analyzed according to Analysis methods 1 and 5 giving the following results.

| | |
|---|---|
| Water dispersion of a capsule having a diameter from 0.3 to 5 μm, mainly from 1 to 2 μm | 370 g |
| Components excepting water | 11.9% |

As described above, in this Example 2M, a microcapusule containing core material was obtained even if a compound having a cationic group was used as a part of monomer components for organopolysiloxane forming the capsule wall.

The microcapsule containing core material obtained in Example 2M was tested if the capsule thereof was broken in the above-described Test method 1 or not. No breakage of the capsule was found.

Example 2N

A microcapsule containing core material was produced in the same manner as in Examples 2 except that 4.6 g of retinol palmitate and 4.6 g of isopropyl isostearate were used instead of 2-ethylhexyl p-methoxycinnamate.

The dispersion of the resulting microcapsule containing core material was analyzed according to Analysis methods 1–5 giving the following results.

| | |
|---|---|
| Water dispersion of a capsule having a diameter from 0.3 to 5 μm, mainly from 1 to 2 μm | 310 g |
| Components excepting water | 14.8% |

The amount of free retinol palmitate in the dispersion was 0.1%.

The amount of retinol palmitate contained in the capsule was 9.9%.

As described above, in this Example 2N, a microcapusule containing retinol palmitate which is viscous at a room temperature was obtained by dissolving retinol palmitate in isopropyl isostearate.

The microcapsule containing core material obtained in Example 2M was tested if the capsule thereof was broken in the above-described Test method 1 or not. No breakage of the capsule was found.

Example 2O

A microcapsule containing core material was produced in the same manner as in Examples 2 except that 4.6 g of tocophenol acetate and 4.6 g of isopropyl isostearate were used instead of 2-ethylhexyl p-methoxycinnamate.

The dispersion of the resulting microcapsule containing core material was analyzed according to Analysis methods 1 and 5 giving the following results.

| | |
|---|---|
| Water dispersion of a capsule having a diameter from 0.3 to 10 $\mu$m, mainly from 2 to 7 $\mu$m | 324 g |
| Components excepting water | 14.3% |

As described above, in this Example 2O, a microcapusule containing tocophenol acetate which is a derivative of vitamin E was obtained by dissolving retinol palmitate in isopropyl isostearate.

The microcapsule containing core material obtained in Example 2O was tested if the capsule thereof was broken according to the above-described Test method 1 or not, to find that a capsule having a particle size of about 8 $\mu$m or more was broken. Particularly, in the condition wherein capsules having a particle size from 8 to 10 $\mu$m were broken, leaking of the core material out of the capsule was observed, and it was observed that the capsule wall and the core material are rounded respectively to form the shape of an "eight". However very little breakage was observed of a capsule having a particle size of less than 8 $\mu$m.

Example 3

A microcapsule containing core material was produced in the same manner as in Examples 2 except that before treatment of trimethylchlorosilane in Examples 2, 3.0 g of 18% hydrochloric acid was previously added to the reaction solution, and 10.6 g of octadecyldimethyl-(3-trimethoxysilylpropyl)ammonium chloride was added and 2.4 g of a 25% aqueous sodium hydroxide solution was added for neutralization.

The dispersion of the resulting microcapsule containing core material was analyzed according to Analysis methods 1 and 5 giving the following results.

| | |
|---|---|
| Water dispersion of a capsule having a diameter from 0.3 to 5 $\mu$m, mainly from 1 to 2 $\mu$m | 820 g |
| Components excepting water | 61.1% |

According to the production process of a microcapsule containing core material in Example 3 except that the addition of octadecyldimethyl-(3-trimethoxysilylpropyl) ammonium chloride and the following series of neutralization treatments and the addition of methyltrichlorosllane and the following series of neutralization treatments were deleted, no difference from the present examples was recognized with the naked eyes, however, microscope observation revealed mutual adhesion of the microcapsule and partial coagulation. However, in the present examples 3, such coagulation was not recognized.

The microcapsule containing core material obtained in Example 3 was tested if the capsule thereof was broken in the above-described Test method 1 or not. No breakage of the capsule was found.

Example 4

Production of a microcapsule containing 2-ethylhexyl p-methoxycinnamate and having a capsule wall made of organopolysiloxane composed of a co-polycondensate of the hydrolysate of N-[2-hydroxy-3-(3'-dihydroxymethylsilyl) propoxy]propyl hydrolyzed collagen, methyltriethoxysilane and phenyltriethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 405 g of water, 45 g of N-[2-hydroxy-3-(3'-dihydroxymethylsilyl)propoxy]propyl hydrolyzed collagen (number-average molecular weight of the hydrolyzed collagen is about 2000) and 10.8 of 18% hydrochloric acid. Thereto, a mixture of 137.7 g of methyltriethoxysilane and 37.1 g of phenyltriethoxysilane was added dropwise from the dropping funnel at 50° C. with stirring.

The mixture was further stirred for 6 hours at 50° C. Then, 8.7 g of a 25% aqueous sodium hydroxide solution was added dropwise with stirring to control the pH to 7.0, and the mixture was further stirred for 1 hour at 50° C.

2) Addition of Core Material and Emulsification 126.9 g of 2-ethylhexyl p-methoxycinnamate was added to the reaction solution prepared in the process 1) with stirring at 600 rpm, and the mixture was further stirred for 4 hours at 600 rpm.

3) Micronization

About a half of the reaction solution prepared in the process 2) was transferred to a vessel of a homomixer, and treated by the homomixer at 50° C. and 6000 rpm for 90 minutes to micronize the components. Further, this treated solution was treated by a microfluidizer [M110-E/H (trade name) manufactured by Microfluidex.International.Corporation] at 50° C. and 1500 kg/cm$^2$ five times, to micronize the components.

4) Prevention of Coagulation and Curing Treatment of Capsule Wall 1.0 g of trimethylchlorosilane was added to the solution prepared in the process 3) in the original reaction vessel with stirring at 600 rpm and 50° C., then, 1.48 g of a 25% aqueous sodium hydroxide solution was added dropwise immediately. The temperature of the reaction solution was raised gradually to reflux. A vapor containing alcohol was distilled off, and the remaining mixture was further heated to reflux with stirring at 150 rpm for 6 hours. This reaction solution was cooled with stirring at 150 rpm at room temperature to obtain a microcapsule containing core material.

The dispersion of the microcapsule containing core material obtained in Example 4 was analysed according to the above-described Analysis methods 1 and Analysis method 6, to obtain the following results. In Example 4, since micronization was conducted using the microfluidizer as described above, the resulting microcapsule containing core material was in the range of nanocapsules. Therefore, regarding the microcapsule containing core material obtained in Example 4, the particle size distribution could not measured by visual observation using the optical microscope according to Analysis method 5, and accordingly, measurement of particle size distribution by SALD-2000 (trade name) in Analysis method 6 was conducted.

| | |
|---|---|
| Water dispersion of a capsule having a diameter from 0.3 to 1 $\mu$m, mainly from 0.4 to 0.7 $\mu$m | 250 g |
| Components excepting water | 20% |

The microcapsule containing core material obtained in Example 4 was tested if the capsule thereof was broken in the above-described Test method 1 or not. No breakage of the capsule was found.

Example 4A

A microcapsule containing core material was produced in the same manner as in Examples 4 except that, in "3) Micronization", remaining half of the reaction solution prepared in the process 2) in Example 4 was used, and the micronization treatment by a microfluidizer was not conducted.

The dispersion of the resulting microcapsule containing core material was analyzed according to Analysis methods 1 and 6 giving the following results.

| | |
|---|---|
| Water dispersion of a capsule having a diameter from 0.3 to 5 µm, mainly from 1 to 2 µm | 250 g |
| Components excepting water | 20% |

The microcapsule containing core material obtained in Example 4A was tested if the capsule thereof was broken in the above-described Test method 1 or not. No breakage of the capsule was found.

Example 5

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 210 g of water, 90 g of N-[2-hydroxy-3-(3'-dihydroxymethylsilyl)propoxy]propyl hydrolyzed collagen (number-average molecular weight of the hydrolyzed collagen is about 2000) and 21.8 g of 18% hydrochloric acid. Thereto, a mixture of 45.9 g of methyltriethoxysilane and 10.5 g of hexyltriethoxysilane was added dropwise from the dropping funnel at 50° C. with stirring.

The mixture was further stirred for 6 hours at 50° C. Then, 22 g of a 25% aqueous sodium hydroxide solution was added dropwise with stirring to control the pH to 7.0, and the mixture was further stirred for 1 hour at 50° C.

2) Addition of Core Material and Emulsification 389 g of 2-ethylhexyl p-methoxycinnamate was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Curing Treatment of Capsule Wall

The solution prepared in the process 3) in the original reaction vessel was further heated to reflux with stirring at 150 rpm for 2 hours. This reaction solution was cooled with stirring at 150 rpm at room temperature to obtain a microcapsule containing core material.

The dispersion of the resulting microcapsule containing core material was analyzed according to Analysis method 5 giving the following results.

Water dispersion of a capsule having a diameter from 0.3 to 5 µm, mainly from 1 to 2 µm 5) Spray-drying A part of the product obtained in the process 4) was spray-dried to give a powder. 0.1 g of this powder was added to 10 ml of water, and the mixture was dispersed by complete stirring, and observed according to Analysis method 5 to find the same observation results as those before the spray-drying.

Example 5A

Freeze-drying Treatment of Microcapsule Containing Core Material

A part of the product obtained in the process 4) of Example 5 was freeze-dried without spray-drying treatment to give a powder. 0.1 g of this powder was added to 10 ml of water, and the mixture was dispersed by complete stirring, and observed according to Analysis method 5 to find the same observation results as those before the spray-drying.

Example 6

Purification Using Centrifugal Separator of Microcapsule Containing Core Material A microcapsule containing core material was produced in the same manner as in Example 2 except that 8.7 g of hexyltrimethoxysilane was used instead of phenyltriethoxysilane in Example 2, 15 g of N-[2-hydroxy-3-(3'-dihydroxymethylsilyl)propoxy]propyl hydrolyzed collagen (number-average molecular weight of hydrolyzed collagen is about 2000) was used instead of N-[2-hydroxy-3-(3'-trihydroxysilyl)propoxy]propyl hydrolyzed collagen, 38.3 g of methyltriethoxysilane was used, 35.3 g of 2-ethylhexyl p-methoxycinnamate was used, and treatment with methyltrichlorosilane was not conducted.

The resulting microcapsule containing core material was centrifuged (4000 rpm, 10 minutes), the supernatant was removed, then, 2 to 5 volumes of water was added to the precipitant and suspended again, then, again centrifuged (4000 rpm, 10 minutes). This operation was repeated three times to obtain a microcapsule containing core material having controlled concentration.

The dispersion of the resulting microcapsule containing core material was analyzed according to Analysis methods 1 and 5 giving the following results.

| | |
|---|---|
| Water dispersion of a capsule having a diameter from 0.3 to 5 µm, mainly from 1 to 2 µm | 150 g |
| Components excepting water | 44% |
| NaCl content in the dispersion before centrifugal separation treatment | 0.34% |
| NaCl content in the dispersion after centrifugal separation treatment | 0.02% |

As described above, it was recognized that NaCl reduces by centrifugal separation treatment.

Example 6A

Purification by Ultrafiltration of Microcapsule Containing Core Material Obtained in Example 2F A part of the microcapsule containing core material obtained in Example 2F was ultrafiltrated, then, 2 to 5 volumes of water was added to the remaining material and dispersed again, then, again ultrafiltrated. This operation was repeated three times to obtain a microcapsule containing core material having controlled concentration.

The dispersion of the resulting microcapsule containing core material was analyzed according to Analysis methods 1 and 5 giving the following results.

| | |
|---|---|
| Water dispersion of a capsule having a diameter from 1 to 10 μm, mainly from 3 to 7 μm | 200 g |
| Components excepting water | 20% |
| NaCl content in the dispersion before ultrafiltration treatment | 0.38% |
| NaCl content in the dispersion after ultrafiltration treatment | 0.03% |

As described above, it was recognized that NaCl reduces by ultrafiltration treatment.

Example 7

Production of a W/O type microcapsule having a capsule wall made of organopolysiloxane composed of a co-polycondensate of the hydrolysate of N-[2-hydroxy-3-(3'-dihydroxymethylsilyl)propoxy]propyl hydrolyzed collagen, dimethyldiethoxysilane and hexyltrimethoxysilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 131 g of water, 9 g of N-[2-hydroxy-3-(3'-dihydroxymethylsilyl)propoxy]propyl hydrolyzed collagen (number-average molecular weight of the hydrolyzed collagen is about 400) and 8 g of 18% hydrochloric acid. Thereto, a mixture of 20.6 g of dimethyldiethoxysilane and 57.3 g of hexyltriethoxysilane was added dropwise from the dropping funnel at 50° C. with stirring.

The mixture was further stirred for 6 hours at 50° C. Then, 6.3 g of a 25% aqueous sodium hydroxide solution was added dropwise with stirring to control the pH to 7.0, and the mixture was further stirred for 1 hour at 50° C.

2) Addition of an Oil Phase and Phase Inversion and Emulsification 150 g of Toluene was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Prevention of Coagulation and Curing Treatment of Capsule Wall 3.0 g of trimethylchiorosilane was added to the solution prepared in the process 3) in the original reaction vessel with stirring at 600 rpm and 50° C., then, 4.4 g of a 25% aqueous sodium hydroxide solution was added dropwise immediately. The temperature of the reaction solution was raised gradually to reflux and 85% of water was distilled off. The remaining mixture was further heated to reflux with stirring at 150 rpm for 6 hours. This reaction solution was cooled with stirring at 150 rpm at room temperature to obtain a microcapsule containing core material.

The dispersion of the resulting microcapsule containing core material was analyzed according to Analysis method 5 giving the following results.

| | |
|---|---|
| Toluene dispersion of a capsule having a diameter from 0.3 to 5 μm, mainly from 1 to 2 μm | 241 g |

The dispersion was applied on a glass plate, and a film formed by evaporation of toluene was scratched to observe water drops on the surface of the glass plate. Further, this dispersion was mixed with water, then, allowed to stand still to find separation into two layers. The capsule dispersed in the toluene layer. From this observation, it was recognized that a microcapsule containing water and having hydrophobic surface could be produced.

Example 7A

A microcapsule containing core material was produced in the same manner as in Example 7 except that the amount of hexyltrimethoxysilane in Example 7 was changed from 573.3 g to 86.0 g; dimethyldiethoxysilane was not used; in the addition of an oil phase and phase inversion and emulsification of the process 2), 160 g of isopropyl isostearate was used instead of toluene used; in the prevention of coagulation and curing treatment of a capsule wall of the process 4), a equimolar of potassium hydroxide was used instead of sodium hydroxide; and 30.8 g of a 35% aqueous potassium chloride solution was added simultaneously in mixing isopropyl isostearate.

The dispersion of the microcapsule containing core material obtained in Example 7A was analyzed according to the above-described Analysis method 5 to find the following result.

| | |
|---|---|
| A dispersion of a capsule having diameter of 0.3 to 5 μm, mainly of 1 to 2 μm in isopropyl isostearate | 280 g |

When the dispersion in Example 7A was mixed with water and allowed to stand still, the mixture was separated into two layers, and the microcapsule containing core material was dispersed in the isopropyl isostearate layer. Thus, a W/O type microcapsule containing core material could be produced without using dialkoxysilane in this Example 7A unlike Example 7.

The microcapsule containing core material obtained in Example 7A was tested if the capsule thereof was broken in the above-described Test method 1 or not. No breakage of the capsule was found.

Example 7B

A microcapsule containing core material was produced in the same manner as in Example 7 except that 71.6 g of hexyltrimethoxysilane and 16.7 g of phenyltriethoxysilane were used instead of dimethyldiethoxysilane and hexyltrimethoxysilane in Example 7, 34.4 g of a 36% L-ascorbic acid aqueous solution was added simultaneously in adding toluene, and 50% of water was distilled off before the treatment by the homomixer.

The dispersion of the microcapsule containing core material obtained in Example 7B was analyzed according to the above-described Analysis method 5 to find the following result.

| Toluene dispersion of a capsule having diameter of 0.3 to 5 μm, mainly of 1 to 2 μm | 216 g |
|---|---|

The dispersion in Example 7B was applied on a glass plate, and a film formed by evaporation of toluene was scratched to observe water drops on the surface of the glass plate. This dispersion was mixed with water, then, allowed to stand still to find separation into two layers and the microcapsule dispersed in the toluene layer.

The microcapsule containing core material obtained in Example 7B was tested if the capsule thereof was broken in the above-described Test method 1 or not. No breakage of the capsule was found.

Example 7C

A microcapsule containing core material was produced in the same manner as in Example 7 except that 235 g of diisobutyladipate was used instead of toluene in Example 7, 106 g of a 10% aqueous solution of 2-phosphoric acid-L-ascorbylmagnesium was added simultaneously in adding this diisobutyladipate, the product was purified by centrifugal separation and treated by the homomixer according to Example 6, then, almost all of water was distilled at 40° C. under reduced pressure, then, the remaining water was distilled off by heating at atmospheric pressure.

The dispersion of the microcapsule containing core material obtained in Example 7C was analyzed according to the above-described Analysis method 5 to find the following result.

| Toluene dispersion of a capsule having diameter of 0.3 to 5 μm, mainly of 1 to 2 μm | 324 g |
|---|---|

200 ml of n-hexane was added to 20 g of the dispersion obtained in Example 7C, extracted with 100 ml of water and measured by a ultraviolet ray-visible light spectral photometer UV-1600 (trade name) manufactured by Shimadzu Corp., to find that 10% of the 2-phosphoric acid-L-ascorbylmagnesium added was liberated. Further, when 50 ml of chloroform was added to 2 g of the dispersion obtained in Example 7C and the mixture was stirred for 1 hour at 50° C., the capsule was broken. This was extracted with 100 ml of water and measured by a ultraviolet ray spectral photometer to find that 95% of the 2-phosphoric acid-L-ascorbylmagnesium added was recovered. As a result, it was known that the intaking ratio was 85%. Further, it has become apparent that free 2-phosphoric acid-L-ascorbylmagnesium can be removed by extraction with water and washing.

When the dispersion in Example 7C was mixed with water and then allowed to stand still, the mixture was separated into two layers, and the microcapsule containing core material was dispersed into the diisobutyladipate layer.

The microcapsule containing core material obtained in Example 7C was tested if the capsule thereof was broken in the above-described Test method 1 or not. No breakage of the capsule was found.

Example 8

Production of microcapsule containing core material of liquid perfluoroether having a capsule wall made of organopolysiloxane composed of a co-polycondensate of the hydrolysate of N-[2-hydroxy-3-(3'-dihydroxymethylsilyl)propoxy]propyl hydrolyzed collagen, tetraethoxysilane and $C_8F_{17}CH_2CH_2Si(OCH_3)_3$ (KBM-7803 manufactured by Shin-Etsu Silicone Co., Ltd.)

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 90 g of water, 10 g of N-[2-hydroxy-3-(3'-dihydroxymethylsilyl)propoxy]propyl hydrolyzed collagen (number-average molecular weight of the hydrolyzed collagen is about 2000) and 2.4 g of 18% hydrochloric acid. Thereto, a mixture of 19.0 g of tetraethoxysilane and 3.2 g of $C_8F_{17}CH_2CH_2Si(OCH_3)_3$ (KBM-7803 manufactured by Shin-Etsu Silicone Co., Ltd.) was added dropwise from the dropping funnel at 50° C. with stirring.

The mixture was further stirred for 12 hours at 50° C. Then, 100 g of a 0.6% aqueous sodium hydroxide solution was added dropwise with stirring to control the pH to 7.0, and the mixture was further stirred for 1 hour at 50° C.

2) Addition of Liquid Perfluoroether and Emulsification

A mixture of 6.8 g of perfluoroether, Fomblin HC/R (manufactured by Moteflous Co., Ltd., average molucular weight of 6250, $CF_3[(OCF(CF_3)CF_2)n(OCF_2)m]OCF_3$, n/m=20–40) and 3.2 g of $C_8F_{17}CH_2CH_2Si(OCH_3)_3$ (KBM-7803 manufactured by Shin-Etsu Silicone Co., Ltd.) was added to the reaction solution prepared in the process 1) with stirring at 500 rpm, and the mixture was further stirred for 4 hours at 500 rpm.

3) Micronization

The reaction solution prepared in the process 2) was transferred to a vessel of a homomixer, and treated by the homomixer at 50° C. and 6000 rpm for 90 minutes to micronize the components.

4) Prevention of Coagulation and Curing Treatment of Capsule Wall 1.23 g of trimethylchlorosilane was added to the solution prepared in the process 3) in the original reaction vessel with stirring at 500 rpm and 50° C., then, 1.2 g of a 25% aqueous sodium hydroxide solution was added dropwise immediately. The temperature of the reaction solution was raised gradually to reflux with stirring at 500 rpm and 50° C. The mixture was further heated to reflux with stirring at 150 rpm for 6 hours. This reaction solution was cooled with stirring at 150 rpm at room temperature to obtain a microcapsule containing core material as a milky white dispersion.

The dispersion of the microcapsule containing core material obtained in Example 8 was analysed according to the above-described Analysis method 1 and Analysis method 5, to obtain the following results.

| Water dispersion of a capsule having a diameter from 5 to 10 μm | 110 g |
|---|---|
| Components excepting water | 17.1% |

This dispersion could be freeze-dried.

The microcapsule containing core material obtained in Example 8 was tested if the capsule thereof was broken according to the above-described Test method 1 or not, to find that a capsule having a particle size of about 8 μm or more was broken. Particularly, in the condition wherein capsules having a particle size from 8 to 10 μm were broken, leaking of the core material out of the capsule was observed, and it was observed that the capsule wall and the core material are rounded respectively to form the shape of an "eight". However very little breakage was observed of a capsule having a particle size of less than 8 μm.

Comparative Example 3
1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 90 g of water, log of N-[2-hydroxy-3-(3'-dihydroxymethylsilyl)propoxy]propyl hydrolyzed collagen (number-average molecular weight of the hydrolyzed collagen is about 2000) and 2.4 g of 18% hydrochloric acid. Thereto, a mixture of 19.0 g of tetraethoxysilane and 9.5 g of $C_8F_{17}CH_2CH_2Si(OCH_3)_3$ (KBM-7803 manufactured by Shin-Etsu Silicone Co., Ltd.) was added dropwise from the dropping funnel at 50° C. with stirring.

The mixture was further stirred for 12 hours at 50° C. Then, 100 g of a 0.6% aqueous sodium hydroxide solution was added dropwise with stirring to control the pH to 7.0, and the mixture was further stirred for 1 hour at 50° C.
2) Addition of Liquid Perfluoroether and Emulsification 6.8 g of perfluoroether, Fomblin HC/R (manufactured by Moteflous Co., Ltd., average molucular weight of 6250, $CF_3[(OCF(CF_3)CF_2)n(OCF_2)m]OCF_3$, n/m=20–40) was added to the reaction solution prepared in the process 1) with stirring at 500 rpm, and the mixture was further stirred for 4 hours at 500 rpm.
3) Micronization The reaction solution prepared in the process 2) was transferred to a vessel of a homomixer, and treated by the homomixer at 50° C. and 6000 rpm for 90 minutes to micronize the components.
4) Prevention of Coagulation and Curing Treatment of Capsule Wall 1.23 g of trimethylchlorosilane was added to the solution prepared in the process 3) in the original reaction vessel with stirring at 500 rpm and 50° C., then, 1.2 g of a 25% aqueous sodium hydroxide solution was added dropwise immediately. The temperature of the reaction solution was raised gradually to reflux with stirring at 500 rpm. The mixture was further heated to reflux with stirring at 150 rpm for 6 hours. This reaction solution was cooled with stirring at 150 rpm at room temperature. This reaction solution split into three phases.

The dispersion of the microcapsule containing core material obtained in this Comparative Example was analysed according to the above-described Analysis method 5, to obtain the following results.

No capsule was observed with the optical microscope.

260 g of liquid separated into three phases was obtained.

The microcapsule containing core material was not obtained in this Comparative Example. However, in Example 8, in which a part of the compound having a perfluoroalkane group, $C_8F_{17}CH_2CH_2Si(OCH_3)_3$ (KBM-7803 manufactured by Shin-Etsu Silicone Co., Ltd.), was added simultaneously in adding the core material, a microcapsule containing a liquid perfluoroether was obtained.

Example 9

Production of microcapsule containing core material of 2-ethylhexyl p-methoxycinnamate having a capsule wall made of organopolysiloxane composed of the hydrolysate co-polycondensate of methyltriethoxysilane and phenyltriethoxysilane in gelatin aqueous solution.
1) Preparation of Prepolymer A 2-liter round bottom cylindrical glass reaction vessel having an internal diameter of 12 cm equipped with a mechanical stirrer, having an upper cover equipped with a mechanical stirrer, having an upper cover equipped with a dropping funnel and a reflux condenser, was charged with 120 g of water, and to this was added 6 g of gelatin as a thickening agent and mixture was heated to dissolve gelatin. The solution was cooled to 20° C., and the viscosity thereof was controlled to 50 mPa·s, 5.5 g of 10% hydrochloric acid was added to this solution to make the solution acidic, then, 12.8 g of phenyltriethoxysilane was added, and the mixture was stirred for 30 minutes at 20° C. Then, 48 g of methyltriethoxysilane was added and the mixture was stirred for 10 minutes to dissolve the ingredient.
2) Addition of Core Material and Emulsification The reaction solution prepared in the process 1) was controlled to pH 7.0 with 25% of aqueous sodium hydroxide solution, then, immediately, lOOg of 2-ethylhexyl p-methoxycinnamate was added to the solution with stirring at 600 rpm to obtain an emulsion.
3) Micronization The reaction solution prepared in the process 2) was stirred at 20° C. for 10 minutes and diluted with 60 g of water. Then, it was treated by the homomixer at 40° C. and 6000 rpm for 60 minutes to micronize the components.
4) Prevention of Coagulation and Curing Treatment of Capsule Wall 1.0 g of hexaethyldisilazane was added to the emulsion prepared in the process 3) with stirring and keeping the emultion at 40° C., then, 1.0 g of a 25% aqueous sodium hydroxide solution was added to control the pH at 7.0. The temperature of the reaction solution was raised gradually to reflux. A vapor containing alcohol was distilled off, and the solution was further heated to reflux with stirring for 6 hours. This reaction solution was cooled to obtain a microcapsule containing core material.
5) Removal of Gelatin and Free 2-ethylhexyl p-methoxycinnamate The dispersion obtained in the process 4) was separated by a centrifugal separator, the supernatant was discarded, and the remaining solution was washed by adding 100 ml of water. The same operation was repeated five times, gelatin and free 2-ethylhexyl p-methoxycinnamate were removed. Finally, 100 ml of water was added to the remainder to obtain a dispersion of a microcapsule containing core material.

The dispersion of the resulting microcapsule containing core material was analyzed according to Analysis methods 1 and 5 giving the following results.

| | |
|---|---|
| Water dispersion of a capsule having a diameter from 1 to 30 μm, mainly from 10 to 20 μm | 200 g |
| Components excepting water | 50% |

In Example 9, a microcapsule containing core material of 2-ethylhexyl p-methoxycinamate having a capsule wall made of organopolysiloxane composed of a hydrolysate poly-condensate of methyltriethoxysilane can be produced in stable manner in a geatin solution.

The microcapsule geatin containing core material obtained in Example 9 was tested if the capsule thereof was broken according to the above-described Test method 1 or not, to find that a capsule having a particle size of about 8 μm or more was broken. Particularly, in the condition wherein capsules having a particle size from 8 to 15 μm were broken, leaking of the core material out of the capsule was observed, and it was observed that the capsule wall and the core material are rounded respectively to form the shape of an "eight". However very little breakage was observed of a capsule having a particle size of less than 8 μm.

Example 10

Production of a microcapsule containing 2-ethylhexyl p-methoxycinnamate and having a capsule wall made of organopolysiloxane composed of a co-polycondensate of the hydrolysate of N-[2-hydroxy-3-(3'-trihydroxysilyl)propoxy]propyl hydrolyzed collagen, methyltriethoxysilane and phenyltriethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 135 g of water, 15 g of N-[2-hydroxy-3-(3'-trihydroxysilyl)propoxy]propyl hydrolyzed collagen (number-average molecular weight of the hydrolyzed collagen is about 2000) and 3.6 g of 18% hydrochloric acid, and a mixture of 45.9 g of methyltriethoxysilane (KBE-13 manufactured by Shin-Etsu Silicone Co., Ltd.) and 12.4 g of phenyltriethoxysilane (KBE-103 manufactured by Shin-Etsu Silicone Co., Ltd.) was dropped from the dropping funnel at 50° C. with stirring.

The mixture was further stirred for 6 hours at 50° C. Then, 2.9 g of a 25% aqueous sodium hydroxide solution was added dropwise with stirring, to control the pH to 7.0.

2) Addition of Core Material and Emulsification

A mixture of 389 g of 2-ethylhexyl p-methoxycinnamate (MCX, manufactured by Nippon Roche K.K.) and 3.9 g of AZ-6101 (Me$_3$SiO(Me$_2$SiO)$_\alpha$[MeSi(EtO)O]$_\beta$SiMe$_3$, manufactured by Nippon Unicar Co., Ltd.) was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes, to micronize the components.

4) Prevention of Coagulation and Curing Treatment of Capsule Wall 3.0 g of trimethylchlorosilane (KA-31, manufactured by Shin-Etsu Silicone Co., Ltd.) was added to the solution prepared in the process 3) in the original reaction vessel with stirring at 250 rpm and 50° C., then, 4.4 g of a 25% aqueous sodium hydroxide solution was added dropwise immediately. The temperature of the reaction solution was raised gradually to reflux. A vapor containing alcohol was distilled off, and the remaining mixture was further heated to reflux with stirring at 150 rpm for 2 hours. This reaction solution was cooled with stirring at 150 rpm at room temperature to obtain a microcapsule containing a core material.

The amount of free 2-ethylhexyl p-methoxycinnamate in the dispersion was 1.58%.

Example 11

A microcapsule containing a core material was produced in the same manner as in Examples 10 except that a mixture of 389 g of 2-ethylhexyl p-methoxycinnamate (MCX, manufactured by Nippon Roche K.K.) and 3.9 g of methylhydrogenpolysiloxane (KF-99P, manufactured by Shin-Etsu Silicone Co., Ltd.) was used instead of a mixture of 389 g of 2-ethylhexyl p-methoxycinnamate and 3.9 g of AZ-6101 (Me$_3$SiO(Me$_2$SiO)$_\alpha$[MeSi(EtO)O]$_\beta$SiMe$_3$, manufactured by Nippon Unicar Co., Ltd.).

The amount of free 2-ethylhexyl p-methoxycinnamate in the dispersion was 1.55%.

Example 12

A microcapsule containing a core material was produced in the same manner as in Examples 10 except that a mixture of 389 g of 2-ethylhexyl p-methoxycinnamate (MCX, manufactured by Nippon Roche K.K.) and 3.9 g of tetraethoxysilane (KBE-04, manufactured by Shin-Etsu Silicone Co., Ltd.) was used instead of a mixture of 389 g of 2-ethylhexyl p-methoxycinnamate and 3.9 g of AZ-6101 (Me$_3$SiO(Me$_2$SiO)$_\alpha$[MeSi(EtO)O]$_\beta$SiMe$_3$, manufactured by Nippon Unicar Co., Ltd.).

The amount of free 2-ethylhexyl p-methoxycinnamate in the dispersion was 1.05%.

Example 13

Production of a microcapsule containing 2-ethylhexyl p-methoxycinnamate and having a capsule wall made of organopolysiloxane composed of a co-polycondensate of the hydrolysate of N-[2-hydroxy-3-(3'-trihydroxysilyl)propoxy]propyl hydrolyzed collagen, methyltriethoxysilane, phenyltriethoxysilane and tetraethoxysilane 1) Preparation of Prepolymer of Capsule Wall A 2-liter round bottom cylindrical glass reaction vessel having an internal diameter of 12 cm equipped with a mechanical stirrer, having an upper cover equipped with a dropping funnel and a reflux condenser, was previously charged 135 g of water, 15 g of N-[2-hydroxy-3-(3'-trihydroxysilyl)propoxy]propyl hydrolyzed collagen (number-average molecular weight of the hydrolyzed collagen is about 2000) and 3.6 g of 18% hydrochloric acid, and a mixture of 45.9 g of methyltriethoxysilane (KBE-13 manufactured by Shin-Etsu Silicone Co., Ltd.), 12.4 g of phenyltriethoxysilane (KBE-103 manufactured by Shin-Etsu Silicone Co., Ltd.) and 3.6 g of tetraethoxysilane (KBE-04 manufactured by Shin-Etsu Silicone Co., Ltd.) was dropped from the dropping funnel at 50° C. with stirring.

The mixture was further stirred for 6 hours at 50° C. Then, 2.9 g of a 25% aqueous sodium hydroxide solution was added dropwise with stirring, to control the pH to 7.0.

2) Addition of Core Material and Emulsification

A mixture of 389 g of 2-ethylhexyl p-methoxycinnamate (MCX, manufactured by Nippon Roche K.K.) and 3.9 g of tetraethoxysilane (KBE-04 manufactured by Shin-Etsu Silicone Co., Ltd.) was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes, to micronize the components.

4) Over Coat Treatment of Capsule Wall

A mixture of 1.28 g of methyltrichlorosilane (KA-13 manufactured by Shin-Etsu Silicone Co., Ltd.) and 6.0 g of methyltriethoxysilane (KBE-13 manufactured by Shin-Etsu Silicone Co., Ltd.) was added to the reaction solution prepared in the process 3) in the original reaction vessel with stirring at 50° C. and 250 rpm, and further, the mixture was stirred for 1 hour at 250 rpm. Then 4.05 g of a 25% aqueous sodium hydroxide solution was added for neutralization. 30 minutes after the neutralization, the same operation was repeated.

5) Prevention of Coagulation and Curing Treatment of Capsule Wall 3.0 g of trimethylchlorosilane (KA-31, manufactured by Shin-Etsu Silicone Co., Ltd.) was added to the solution prepared in the process 4) in the original reaction vessel with stirring at 250 rpm and 50° C., then, 4.4 g of a 25% aqueous sodium hydroxide solution was added dropwise immediately. The temperature of the reaction solution was raised gradually to reflux. A vapor containing alcohol was distilled off, and the remaining mixture was further heated to reflux with stirring at 150 rpm for 2 hours. This reaction solution was cooled with stirring at 150 rpm at room temperature to obtain a microcapsule containing a core material.

The amount of free 2-ethylhexyl p-methoxycinnamate in the dispersion was 0.20%.

Example 13A

A microcapsule containing a core material was produced in the same manner as in Examples 13 except that tetraethoxysilane was not used.

The amount of free 2-ethylhexyl p-methoxycinnamate in the dispersion was 2.36%.

Example 14

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed sericin, methyltriethoxysilane, phenyltriethoxysilane and tetraethoxysilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 115.2 g of water, 12.8 g of N-[2-hydroxy-3-(3'-trihydroxysilyl)propoxy]propyl hydrolyzed sericin (number-average molecular weight of the hydrolyzed sericin is about 2000) and 5.0 g of 18% hydrochloric acid, and a mixture of 27.0 g of methyltriethoxysilane (KBE-13 manufactured by Shin-Etsu Silicone Co., Ltd.), 7.3 g of phenyltriethoxysilane (KBE-103 manufactured by Shin-Etsu Silicone Co., Ltd.) and 2.1 g of tetraethoxysilane was dropped from the dropping funnel at 50° C. with stirring.

The mixture was further stirred for 5 hours at 50° C. Then, 4.4 g of a 25% aqueous sodium hydroxide solution was added dropwise with stirring, to control the pH to 7.0.

2) Addition of Core Material and Emulsification

A mixture of 244 g of 2-ethylhexyl p-methoxycinnamate (MCX, manufactured by Nippon Roche K.K.) and 2.44 g of tetraethoxysilane (KBE-04 manufactured by Shin-Etsu Silicone Co., Ltd.) was added to the reaction solution prepared in the process 1), which was cooled to 20° C., with stirring at 700 rpm, and the mixture was further stirred for 4 hours at 700 rpm.

3) Micronization

The reaction solution prepared in the process 2) was transferred to a vessel of a homomixer, and treated by the homomixer at 50° C. and 5000 rpm for 60 minutes, to micronize the components.

4) Over Coat Treatment of Capsule Wall

A mixture of 0.76 g of methyltrichlorosilane (KA-13 manufactured by Shin-Etsu Silicone Co., Ltd.) and 3.6 g of methyltriethoxysilane (KBE-13 manufactured by Shin-Etsu Silicone Co., Ltd.) was added to the reaction solution prepared in the process 3) in the original reaction vessel with stirring at 50° C. and 350 rpm. Then 5.0 g of a 25% aqueous sodium hydroxide solution was added.

5) Prevention of Coagulation and Curing Treatment of Capsule Wall 1.1 g of trimethylchlorosilane (KA-31, manufactured by Shin-Etsu Silicone Co., Ltd.) was added to the solution prepared in the process 4) in the original reaction vessel with stirring at 400 rpm and 50° C., then, 2.3 g of a 25% aqueous sodium hydroxide solution was added dropwise after stirring for 1 hour. The temperature of the reaction solution was raised gradually to reflux. A vapor containing alcohol was distilled off, and the remaining mixture was further heated to reflux with stirring at 250 rpm for 2 hours. This reaction solution was cooled with stirring at 150 rpm at room temperature to obtain a microcapsule containing core material.

The amount of free 2-ethylhexyl p-methoxycinnamate in the dispersion was 0.16%.

After leaving this dispersion for 1 day, the amount of free 2-ethylhexyl p-methoxycinnamate in the dispersion was measured and it was 0.63%.

Example 15

A microcapsule containing core material was produced in the same manner as in Examples 14 except that 2.44 g of tetraethoxysilane (KBE-04, manufactured by Shin-Etsu Silicone Co., Ltd.) was not added.

The amount of free 2-ethylhexyl p-methoxycinnamate in the dispersion was 1.35%.

After leaving this dispertion for 1 day, the amount of free 2-ethylhexyl p-methoxycinnamate in the dispersion was measured and it was 1.61%.

Example 16

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed sericin, methyltriethoxysilane, hexyltrimethoxysilane and tetraethoxysilane.

A microcapsule containing core material was produced in the same manner as in Examples 14 except that the amounts of 2-ethylhexyl p-methoxycinnamate and tetraethylsilane, added as the core materials, were changed to 266 g and 2.66 g, respectively; 7.3 g of phenyltriethoxysilane was replaced with 6.3 g of hexyltrimethoxylsilane (KBM-3063C, manufactured by Shin-Etsu Silicone Co., Ltd.); and the amounts of the 25% aqueous sodium hydroxide solution were changed from 4.4 g, 5.0 g and 2.3 g to 5.4 g, 4.8 g and 3.6 g, respectively.

The amount of free 2-ethylhexyl p-methoxycinnamate in the dispersion was 0.38%.

Example 17

A microcapsule containing core material was produced in the same manner as in Examples 16 except that 2.44 g of tetraethoxysilane (KBE-04, manufactured by Shin-Etsu Silicone Co., Ltd.) was not added to the core material.

The amount of free 2-ethylhexyl p-methoxycinnamate in the dispersion was 1.34%.

Example 18

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed collagen, methyltriethoxysilane, phenyltriethoxysilane and tetraethylsilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged 180 g of water, 20 g of N-[2-hydroxy-3-(3'-trihydroxysilyl)propoxy]propyl hydrolyzed collagen (number-average molecular weight of the hydrolyzed collagen is about 2000) and 4.8 g of 18% hydrochloric acid, and a mixture of 61.2 g of methyltriethoxysilane (KBE-13 manufactured by Shin-Etsu Silicone Co., Ltd.), 16.5 g of phenyltriethoxysilane (KBE-103 manufactured by Shin-Etsu Silicone Co., Ltd.) and 4.8 g of tetraethoxysilane was dropped from the dropping funnel at 50° C. with stirring.

The mixture was further stirred for 4 hours at 50° C. Then, 3.8 g of a 25% aqueous sodium hydroxide solution was added dropwise with stirring, to control the pH to 7.0.

2) Addition of Core Material and Emulsification

A mixture of 69.7 g of 2-ethylhexyl p-methoxycinnamate (MCX, manufactured by Nippon Roche K.K.) and 0.697 g of tetraethoxysilane(KBE-04 manufactured by Shin-Etsu Silicone Co., Ltd.) was added to the reaction solution prepared in the process 1) with stirring at 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes, to micronize the components.

4) Overcoat Treatment

A mixture of 1.7 g of methyltrichlorosilane (KA-13, manufactured by Shin-Etsu Silicone Co., Ltd.) and 8.15 g of methyltriethoxysilane (KBE-13, manufactured by Shin-Etsu Silicone Co., Ltd.) was added to the solution prepared in the process 3) in the original reaction vessel with stirring at 250 rpm and 50° C. After stirring for one hour, 5.46 g of a 25% aqueous sodium hydroxide solution was added dropwise.

After stirring further 30 minutes, a mixture of 1.7 g of methyltrichlorosilane (KA-13, manufactured by Shin-Etsu Silicone Co., Ltd.) and 8.15 g of methyltriethoxysilane (KBE-13, manufactured by Shin-Etsu Silicone Co., Ltd.) was added to the resulting solution, once more. Thereafter, the resulting solution was stirred for one more hour, then 5.46 g of a 25% aqueous sodium hydroxide solution was added dropwise.

5) Prevention of Coagulation and Curing Treatment of Capsule Wall 5.0 g of trimethylchlorosilane (KA-31, manufactured by Shin-Etsu Silicone Co., Ltd.) was added to the solution prepared in the process 4) in the original reaction vessel with stirring at 600 rpm and 50° C., then, 7.36 g of a 25% aqueous sodium hydroxide solution was added dropwise after stirring for 1 hour. The temperature of the reaction solution was raised gradually to reflux. A vapor containing alcohol was distilled off, and the remaining mixture was further heated to reflux with stirring at 250 rpm for 2 hours. This reaction solution was cooled with stirring at 150 rpm at room temperature to obtain a microcapsule containing core material.

The amount of free 2-ethylhexyl p-methoxycinnamate in the dispersion was 0.06%.

After leaving this dispersion for 1 day, the amount of free 2-ethylhexyl p-methoxycinnamate in the dispersion was measured and it was 0.39%.

Example 19

A microcapsule containing core material was produced in the same manner as in Examples 18 except that 0.697 g of tetraethoxysilane (KBE-04, manufactured by Shin-Etsu Silicone Co., Ltd.) was not added.

The amount of free 2-ethylhexyl p-methoxycinnamate in the dispersion was 0.13%.

After leaving this dispersion for 1 day, the amount of free 2-ethylhexyl p-methoxycinnamate in the dispersion was measured and it was 0.77%.

Example 20

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed collagen, methyltriethoxysilane, hexyltrimethoxysilane and tetraethoxysilane.

A microcapsule containing core material was produced in the same manner as in Examples 18 except that the amounts of 2-ethylhexyl p-methoxycinnamate and tetraethylsilane, added as the core materials, were changed to 70.3 and 0.703 g, respectively; and 16.5 g of phenyltriethoxysilane was replaced with 14.15 g of hexyltrimethoxylsilane.

The amount of free 2-ethylhexyl p-methoxycinnamate in the dispersion was 0.13%.

After leaving this dispersion for 1 day, the amount of free 2-ethylhexyl p-methoxycinnamate in the dispersion was measured and it was 0.63%.

Example 21

A microcapsule containing core material was produced in the same manner as in Examples 20 except that 0.703 g of tetraethoxysilane (KBE-04, manufactured by Shin-Etsu Silicone Co., Ltd.) was not added to the core material.

The amount of free 2-ethylhexyl p-methoxycinnamate in the dispersion was 0.15%.

After leaving this dispersion for 1 day, the amount of free 2-ethylhexyl p-methoxycinnamate in the dispersion was measured and it was 1.00%.

Analysis Method 7

0.1 g of the resulting dispersion of the microcapsule containing core material is weighed into a screw tumber having a diameter of 27 mm and a height of 55 mm, and about 5 mL of water is added. to this is added 10 mL of n-hexane and the tube is capped, the center portion is immediately fixed in a horizontal direction and is allowed to rotate with the rotation symmetry axis kept vertical using a motor at 150 rpm, to extract free 2-ethylhexylp-methoxycinnamate. After rotation for 2 minutes, 100 µl of a hexane layer is transferred into a 10 ml measuring flask by a micropipetter, and n-hexane is added to a weighing line. This is called sample A. The tumber is further rotated for 2 minutes and the same treatment is conducted. This is called sample B. The concentration of 2-ethylhexyl p-methoxycinnamate of the sample A and the sample B is measured using liquid chromatography. If the measurement result of the sample A is named a and the measurement result of the sample B is named b, the difference between the analysis result b and the analysis result a (b–a) can be regarded as bleeding amount over 2 minutes. The measurement result a also include the bleeding amount over 2 minutes, i.e. (b–a), together with the amount of free portion, therefore, a-(b−a) can be regarded as the amount of the free 2-ethylhexyl p-methoxycinnamate.

Example 22

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed sericin, methyltriethoxysilane, phenyltriethoxysilane and tetraethoxysilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged with 90 g of water, 10 g of N-[2-hydroxy-3-(3'-trihydroxysilyl)propoxy]propyl hydrolyzed sericin (number-average molecular weight of the hydrolyzed sericin is about 2000) and 3.6 g of 18% hydrochloric acid, and a mixture of 24 g of methyltriethoxysilane (KBE-13 manufactured by Shin-Etsu Silicone Co., Ltd.), 6.45 g of phenyltriethoxysilane (KBE-103 manufactured by Shin-Etsu Silicone Co., Ltd.) and 1.86 g of tetraethoxysilane was dropped from the dropping funnel at 50° C. with stirring.

The mixture was further stirred for 4 hours at 50° C., then cooled to 20° C. Then, 2.45 g of a 25% aqueous sodium hydroxide solution was added dropwise with stirring, to control the pH to 7.0.

2) Addition of Core Material and Emulsification

After stirring the reaction solution prepared in the process 1) for 30 minutes, a mixture of 257.4 g of 2-ethylhexyl p-methoxycinnamate (MCX, manufactured by Nippon Roche K.K.) and 2.6 g of tetraethoxysilane (KBE-04 manufactured by Shin-Etsu Silicone Co., Ltd.) was added thereto with stirring at 20° C. and 600 rpm, and the mixture was further stirred for 4 hours at 600 rpm.

3) Micronization

The reaction solution prepared in the process 2) was transferred to a vessel of a homomixer, and treated by the homomixer at 50° C. and 6000 rpm for 90 minutes. Then, the resulting solution was trasfered to the original reaction vessel and stirred at 50° C. and 600 rpm for 14 hours. Thereafter, the resulting mixture was transferred to the vessel of a homomixer again and treated by the homomixer at 50° C. and 6000 rpm for 60 minutes to micronize the components.

4) Over Coat Treatment of Capsule Wall

A mixture of 0.67 g of methyltrichlorosilane (KA-13 manufactured by Shin-Etsu Silicone Co., Ltd.) and 3.2 g of methyltriethoxysilane (KBE-13 manufactured by Shin-Etsu Silicone Co., Ltd.) was added to the reaction solution prepared in the process 3) in the original reaction vessel with stirring at 50° C. and 250 rpm and the resulting mixture was stirred at 250 rpm for 1 more hour. Then 2.2 g of a 25% aqueous sodium hydroxide solution was added for neutralization.

5) Prevention of Coagulation and Curing Treatment of Capsule Wall 2.0 g of trimethylchlorosilane (KA-31, manufactured by Shin-Etsu Silicone Co., Ltd.) was added to the solution prepared in the process 4) with stirring at 250 rpm and 50° C., then, 2.8 g of a 25% aqueous sodium hydroxide solution was added dropwise after stirring for 1 hour. The temperature of the reaction solution was raised gradually to reflux. A vapor containing alcohol was distilled off, and the remaining mixture was further heated to reflux with stirring at 150 rpm for 2 hours. This reaction solution was cooled with stirring at 150 rpm at room temperature to obtain a microcapsule containing core material.

The dispersion of the resulting microcapsule containing core material was analyzed according to Analysis methods 5 and 7 giving the following results.

Water dispersion of a capsule having a diameter from 0.3 to 5 μm, mainly from 1 to 3 μm.

The amount of free 2-ethylhexyl p-methoxycinnamate in the dispersion was 1.686%.

The amount of 2-ethylhexyl p-methoxycinnamate which leaked in 2 minutes was 0.1138%.

Example 22A

A microcapsule containing core material was produced in the same manner as in Example 22 except that the prepolymer was prepared without using tetraethoxysilane.

Water dispersion of a capsule having a diameter from 1 to 5 μm.

The amount of free 2-ethylhexyl p-methoxycinnamate in the dispersion was 0.210%.

The leaking speed of 2-ethylhexyl p-methoxycinnamate was 0.0348%/minute.

Example 23

1)

The processes, "Preparation of prepolymer of capsule wall" and "Addition of core material and emulsification", were conducted in the same manner as in Example 22.

2) Micronization

The reaction solution prepared in the process 1) was transferred to a vessel of a homomixer, and treated by the homomixer at 50° C. and 6000 rpm for 90 minutes.

3)

The processes, "Over coat treatment of capsule wall" and "Prevention of coagulation and curing treatment of capsule wall", were conducted in the same manner as in Examples 22 to obtain a microcapsule containing core material.

The dispersion of the resulting microcapsule containing core material was analyzed according to Analysis methods 5 and 7 giving the following results.

Water dispersion of a capsule having a diameter from 0.3 to 5 μm, mainly from 1 to 3 μm.

The amount of free 2-ethylhexyl p-methoxycinnamate in the dispersion was 0.7767%.

The amount of 2-ethylhexyl p-methoxycinnamate which leaked in 2 minutes was 0.3801%.

Example 24

1) Preparation of Prepolymer of Capsule Wall

The process, "Preparation of prepolymer of capsule wall"", was conducted in the same manner as in Example 22 except that the amounts of methyltriethoxysilane, phenyltriethoxysilane, tetraethylsilane and 25% aqueous sodium hydroxide solution were changed to 21.6 g, 5.73 g, 1.67 g and 2.2 g, respectively. Since the amount of the 25% aqueous sodium hydroxide solution was 2.2 g, the pH of the resulting solution was not controlled at 7.0.

2) Addition of Core Material and Emulsification

The process, "Addition of core material and emulsification", was conducted in the same manner as in Example 22, except that the amounts of 2-ethylhexyl p-methoxycinnamate and tetraethylsilane were changed to 228.2 g and 2.3 g, respectively.

3) Micronization

Micronization was conducted about the reaction solution prepared in the process 2) in the same manner as in Example 22.

4) Over Coat Treatment of Capsule Wall 0.25 g of a 25% aqueous sodium hydroxide solution was dropwise added to the reaction solution prepared in the process 3) with stirring at 50° C. and 250 rpm. Then, a mixture of 0.585 g of methyltrichlorosilane (KA-13 manufactured by Shin-Etsu Silicone Co., Ltd.) and 2.78 g of methyltriethoxysilane (KBE-13 manufactured by Shin-Etsu Silicone Co., Ltd.) was added thereto and the resulting mixture was stirred for 1 more hour. Thereto, 1.9 g of a 25% aqueous sodium hydroxide solution was added for neutralization.

5) Prevention of Coagulation and Curing Treatment of Capsule Wall

"Prevention of coagulation and curing treatment of capsule wall" was conducted about the reaction solution prepared in the process 4) in the same manner as in Example 22, except that the amounts of trimethylchlorosilane and 25% aqueous sodium hydroxide solution were changed to 1.2 g and 1.7 g, respectively to obtain a microcapsule containing core material.

The dispersion of the resulting microcapsule containing core material was analyzed according to Analysis methods 5 and 7 giving the following results.

| | |
|---|---|
| Water dispersion of a capsule having a diameter from 1 to 5 µm. | |
| Components excepting water | 64.7% |

The amount of free 2-ethylhexyl p-methoxycinnamate in the dispersion was 0.818%.

The leaking speed of 2-ethylhexyl p-methoxycinnamate was 0.0551%/minute.

Example 25

1) Preparation of Prepolymer of Capsule Wall

The process, "Preparation of prepolymer of capsule wall", was conducted in the same manner as in Example 22 except that tetraethoxysilane was not added and 4.0 g of propylene glycol was added after the pH was controlled to 7.0.

2) Addition of Core Material and Emulsification

The process, "Addition of core material and emulsification", was conducted in the same manner as in Example 22, except that the amounts of 2-ethylhexyl p-methoxycinnamate and tetraethylsilane were changed to 250 g and 2.5 g, respectively.

3) Micronization

Micronization was conducted about the reaction solution prepared in the process 2) in the same manner as in Example 22, except that the rotation speed of the homomixer was changed to 8000 rpm.

4)

The processes, "Over coat treatment of capsule wall" and "Prevention of coagulation and curing treatment of capsule wall", were conducted about the reaction solution prepared in the process 3) in the same manner as in Example 22 to obtain a microcapsule containing core material.

The dispersion of the resulting microcapsule containing core material was analyzed according to Analysis methods 5 and 7 giving the following results.

Water dispersion of a capsule having a diameter from 0.3 to 3 µm, mainly from 1 to 3 µm.

The amount of free 2-ethylhexyl p-methoxycinnamate in the dispersion was 0.7994%.

The amount of 2-ethylhexyl p-methoxycinnamate which leaked in 2 minutes was 0.2722%.

Example 26

A microcapsule containing core material was produced in the same manner as in Example 25 except that 4.0 g of propylene glycol was replaced with 4.0 g of glycerin.

The dispersion of the resulting microcapsule containing core material was analyzed according to Analysis methods 5 and 7 giving the following results.

Water dispersion of a capsule having a diameter from 0.3 to 3 µm, mainly from 1 to 3 µm.

The amount of free 2-ethylhexyl p-methoxycinnamate in the dispersion was 0.7028%.

The amount of 2-ethylhexyl p-methoxycinnamate which leaked in 2 minutes was 0.0219%.

Example 27

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl hydrolyzed sericin, methyltriethoxysilane and octyltriethoxysilane.

A microcapsule containing core material was produced in the same manner as in Example 25 except that 6.45 g of phenyltriethoxysilane was replaced with 7.5 g of octyltriethoxysilane (A-137 manufactured by Nippon UniCar Co., Ltd.).

The dispersion of the resulting microcapsule containing core material was analyzed according to Analysis methods 5 and 7 giving the following results.

Water dispersion of a capsule having a diameter from 0.3 to 3 µm, mainly from 1 to 3 µm.

The amount of free 2-ethylhexyl p-methoxycinnamate in the dispersion was 0.4925%.

The amount of 2-ethylhexyl p-methoxycinnamate which leaked in 2 minutes was 0.0695%.

Example 28

Production of a microcapsule containing 2-ethylhexyl p-methoxycinnamate and 4-tert-butyl-4'-methoxydibenzoylmethane and having a capsule wall made of organopolysiloxane composed of a co-polycondensate of the hydrolysate of N-[2-hydroxy-3-(3'-trihydroxysilyl) propoxy]propyl hydrolyzed sericin, methyltriethoxysilane and phenyltriethoxysilane.

1) Preparation of Prepolymer of Capsule Wall

A 2-liter round bottom cylindrical glass reaction vessel having an internal diameter of 12 cm equipped with a mechanical stirrer, having an upper cover equipped with a dropping funnel and a reflux condenser, was previously charged with 90 g of water, 10 g of N-[2-hydroxy-3-(3'-trihydroxysilyl)propoxy]propyl hydrolyzed sericin (number-average molecular weight of the hydrolyzed sericin is about 2000) and 4.0 g of 18% hydrochloric acid, and a mixture of 24.3 g of methyltriethoxysilane (KBE-13 manufactured by Shin-Etsu Silicone Co., Ltd.) and 6.6 g of phenyltriethoxysilane (KBE-103 manufactured by Shin-Etsu Silicone Co., Ltd.) was dropped from the dropping funnel at 50° C. with stirring.

The mixture was further stirred for 4 hours at 50° C., then, 4.0 g of a 20% aqueous sodium hydroxide solution and 1.0 g of EDTA-2Na dispersed in 40 g of water were added dropwise with stirring, followed by addition of 20 g of ethanol, to control the pH to 7.0.

2) Addition of Core Material, Emulsification and Micronization

The reaction solution prepared in the process 1) was transferred to a vessel of a homomixer, and treated by the homomixer at 50° C. and 9000 rpm for 90 minutes with dropwise adding a mixture of 203 g of 2-ethylhexyl p-methoxycinnamate (MCX, manufactured by Nippon Roche K.K.), 50.8 g of 4-tert-butyl-4'-methoxydibenzoylmethane(manufactured by Nippon Roche K.K.) and 2.5 g of tetraethoxysilane (KBE-04 manufactured by Shin-Etsu Silicone Co., Ltd.), to micronize the components.

Then, the resulting solution was trasferred to the original reaction vessel and stirred at 50° C. and 600 rpm. Thereafter, the resulting mixture was transferred to the vessel of a homomixer again and treated by the homomixer at 50° C. and 6000 rpm for 60 minutes to micronize the components.

3) Over Coat Treatment of Capsule Wall

A mixture of 0.68 g of methyltrichlorosilane (KA-13 manufactured by Shin-Etsu Silicone Co., Ltd.) and 3.24 g of methyltriethoxysilane (KBE-13 manufactured by Shin-Etsu Silicone Co., Ltd.) was dropwise added to the reaction solution prepared in the process 2) in the original reaction vessel with stirring at 50° C. and 400 rpm and the resulting mixture was stirred for 1 more hour. Then 2.7 g of a 20% aqueous sodium hydroxide solution was dropwise added.

5) Prevention of Coagulation and Curing Treatment of Capsule Wall 2.0 g of trimethylchlorosilane (KA-31, manufactured by Shin-Etsu Silicone Co., Ltd.) was added to the solution prepared in the process 4) with stirring at 400 rpm and 50° C., then, 3.7 g of a 20% aqueous sodium hydroxide solution was added dropwise after stirring for 1 hour. The temperature of the reaction solution was raised gradually to reflux. A vapor containing alcohol was distilled off, and the remaining mixture was further heated to reflux with stirring at 400 rpm for 2 hours. This reaction solution was cooled with stirring at 150 rpm at room temperature to obtain a microcapsule containing core material.

The dispersion of the resulting microcapsule containing core material was analyzed according to Analysis methods 5 and 7 giving the following results.

| | |
|---|---|
| Water dispersion of a capsule having a diameter from 1 to 20 μm, mainly from 1 to 3 μm | 436.0 g |
| Components excepting water | 60.72% |

The amount of free 2-ethylhexyl p-methoxycinnamate in the dispersion was 0.5658%.

The leaking speed of 2-ethylhexyl p-methoxycinnamate was 0.0427%/minute.

Example 29

A microcapsule containing core material was produced in the same manner as in Examples 28 except that 20 g of ethanol was replaced with 4.5 g of glycerin.

The dispersion of the resulting microcapsule containing core material was analyzed according to Analysis methods 5 and 7 giving the following results.

| | |
|---|---|
| Water dispersion of a capsule having a diameter from 1 to 10 μm, mainly from 1 to 3 μm | 460 g |
| Components excepting water | 60.13% |

The amount of free 2-ethylhexyl p-methoxycinnamate in the dispersion was 0.5151%.

The leaking speed of 2-ethylhexyl p-methoxycinnamate was 0.0254%/minute.

Example 30

A microcapsule containing core material was produced in the same manner as in Examples 28 except that a mixture of 1.0 g of EDTA-2Na dispersed in 40 g of water and 4.5 g of propyleneglycol was added instead of that of 1.0 g of EDTA-2Na dispersed in 40 g of water, then 20 g of ethanol was added.

The dispersion of the resulting microcapsule containing core material was analyzed according to Analysis methods 5 and 7 giving the following results.

| | |
|---|---|
| Water dispersion of a capsule having a diameter from 1 to 15 μm, mainly from 1 to 3 μm | 466.2 g |
| Components excepting water | 59.8% |

The amount of free 2-ethylhexyl p-methoxycinnamate in the dispersion was 0.1848%.

The leaking speed of 2-ethylhexyl p-methoxycinnamate was 0.0192%/minute.

Example 31

A microcapsule containing core material was produced in the same manner as in Examples 28 except that a mixture of 1.0 g of EDTA-2Na dispersed in 40 g of water and 4.5 g of 1,3-butyleneglycol was added instead of that 1.0 g of EDTA-2Na dispersed in 40 g of water, then 20 g of ethanol was added.

The dispersion of the resulting microcapsule containing core material was analyzed according to Analysis methods 5 and 7 giving the following results.

| | |
|---|---|
| Water dispersion of a capsule having a diameter from 1 to 20 μm, mainly from 1 to 3 μm | 460.4 g |
| Components excepting water | 60.7% |

The amount of free 2-ethylhexyl p-methoxycinnamate in the dispersion was 0.5317%.

The leaking speed of 2-ethylhexyl p-methoxycinnamate was 0.0391%/minute.

Example 32

A microcapsule containing core material was produced in the same manner as in Examples 28 except that the amounts of methyltriethoxysilane and phenyltriethoxysilane were changed to 16.2 g and 4.4 g, respectively.

The dispersion of the resulting microcapsule containing core material was analyzed according to Analysis methods 5 and 7 giving the following results.

| | |
|---|---|
| Water dispersion of a capsule having a diameter from 1 to 10 μm, mainly from 1 to 3 μm | 394.0 g |
| Components excepting water | 58.4% |

The amount of free 2-ethylhexyl p-methoxycinnamate in the dispersion was 0.5477%.

The leaking speed of 2-ethylhexyl p-methoxycinnamate was 0.0088%/minute.

Example 33

Production of a microcapsule containing 2-ethylhexyl p-methoxycinnamate and 4-tert-butyl-4'-methoxydibenzoylmethane and having a capsule wall made of organopolysiloxane composed of a co-polycondensate of the hydrolysate of N-[2-hydroxy-3-(3'-trihydroxysilyl)

propoxy]propyl hydrolyzed sericin, methyltriethoxysilane and octyltriethoxysilane.

A microcapsule containing core material was produced in the same manner as in Examples 30 except that 6.6 g of phenyltriethoxysilane was replaced with 7.5 g of octyltriethoxysilane (A-137 manufactured by Nippon UniCar Co., Ltd.).

The dispersion of the resulting microcapsule containing core material was analyzed according to Analysis methods 5 and 7 giving the following results.

| | |
|---|---|
| Water dispersion of a capsule having a diameter from 1 to 15 μm | 463.9 g. |
| Components excepting water | 60.27% |

The amount of free 2-ethylhexyl p-methoxycinnamate in the dispersion was 1.5579%.

The leaking speed of 2-ethylhexyl p-methoxycinnamate was 0.3406%/minute.

Example 34

1)

The processes, "1) Preparation of prepolymer of capsule wall" and "2) Addition of core material and emulsification", were conducted in the same manner as in Examples 30.

2) Addition of Core Material, Emulsification and Micronization

The reaction solution prepared in the process 1) was transferred to a vessel of a homomixer, and treated by the homomixer at 50° C. and 9000 rpm for 90 minutes with dropwise adding a mixture of 203 g of 2-ethylhexyl p-methoxycinnamate (MCX, manufactured by Nippon Roche K.K.), 50.8 g of 4-tert-butyl-4'-methoxydibenzoylmethane(manufactured by Nippon Roche K.K.) and 2.5 g of tetraethoxysilane (KBE-04 manufactured by Shin-Etsu Silicone Co., Ltd.) under a reduced pressure (500 mmHg) to micronize the components.

Then, the resulting solution was trasferred to the original reaction vessel and stirred at 50° C. and 600 rpm. Thereafter, the resulting mixture was transferred to the vessel of homomixer again and treated by the homomixer at 50° C. and at 6000 rpm for 60 minutes to micronize the components.

3)

The processes, "Over coat treatment of capsule wall" and "Prevention of coagulation and curing treatment of capsule wall", were conducted in the same manner as in Examples 30 to obtain a microcapsule containing core material.

The dispersion of the resulting microcapsule containing core material was analyzed according to Analysis methods 5 and 7 giving the following results.

| | |
|---|---|
| Water dispersion of a capsule having a diameter from 1 to 20 μm, mainly from 1 to 3 μm | 466.1 g. |
| Components excepting water | 59.55% |

The amount of free 2-ethylhexyl p-methoxycinnamate in the dispersion was 0.5812%.

The leaking speed of 2-ethylhexyl p-methoxycinnamate was 0.1262%/minute.

Example 35

1) A Prepolymer was Prepared in the Same Manner as in Example 30

2) Addition, Emulsification and Micronization of Core Material

The reaction solution prepared in the process 1) was transferred to a vessel of a homomixer. Thereto, a mixture of 203 g of 2-ethylhexyl p-methoxycinnamate (MCX manufactured by Nippon Roche K.K.), 50.8 g of 4-tert-butyl-4'-methoxydibenzoylmethane (manufactured by Nippon Roche K.K.) and 2.5 g of tetraethoxysilane (KBE-04 manufactures by Shin-Etsu Silicon Co., Ltd) was added dropwise while the solution was being treated by the homomixer at 9000 rpm for 90 minutes in ultrasonic wave (200 W) at 50° C., to be micronized. Then, the reaction solution was stirred at 600 rpm at 50° C. in the original reaction vessel. Then, the reaction solution was again transferred to the vessel of the homomixer, and treated by the homomixer at 6000 rpm and 50° C. for 60 minutes to be micronized.

3)

The processes, "Over coat treatment of capsule wall" and "Prevention of coagulation and curing treatment of capsule wall", were conducted in the same manner as in Examples 30 to obtain a microcapsule containing core material.

The dispersion of the resulting microcapsule containing core material was analyzed according to Analysis methods 5 and 7 giving the following results.

| | |
|---|---|
| Water dispersion of a capsule having a diameter from 1 to 20 μm, mainly from 1 to 3 μm | 445.9 g. |
| Components excepting water | 60.48% |

The amount of free 2-ethylhexyl p-methoxycinnamate in the dispersion was 0.7385%.

The leaking speed of 2-ethylhexyl p-methoxycinnamate was 0.0147%/minute.

Example 36

1) Preparation of Prepolymer of Capsule Wall

The process, "1) Preparation of prepolymer of capsule wall", was conducted in the same manner as in Examples 28 except that 2.4 g of tetraethoxysilane(KBE-04 manufactured by Shin-Etsu Silicone Co., Ltd.) was added and 20 g of ethanol was not added after the pH was controlled to 7.0.

2) Addition of Core Material and Emulsification

A mixture of 202.64 g of 2-ethylhexyl p-methoxycinnamate (MCX, manufactured by Nippon Roche K.K.) and 50.66 g of 4-tert-butyl-4'-methoxydibenzoylmethane (manufactured by Nippon Roche K.K.) was added to the reaction solution prepared in the process 1) with stirring at 600 rpm, then the resulting solution was stirred at 600 rpm for 2 hours.

3) Micronization

The reaction solution prepared in the process 2) was transferred to the vessel of homomixer and treated by the homomixer at 50° C. and 6000 rpm for 90 minutes. Then, the resulting solution was trasferred to the original reaction vessel and stirred at 50° C. and 600 rpm for 15 hours. Thereafter, the resulting mixture was transferred to the vessel of the homomixer again and treated by the homomixer at 50° C. and 6000 rpm for 60 minutes to micronize the components.

4)

The processes, "Over coat treatment of capsule wall" and "Prevention of coagulation and curing treatment of capsule wall", were conducted in the same manner as in Examples 30 to obtain a microcapsule containing core material.

The dispersion of the resulting microcapsule containing core material was analyzed according to Analysis methods 5 and 7 giving the following results.

| | |
|---|---|
| Water dispersion of a capsule having a diameter from 2 to 20 μm | |
| Components excepting water | 59.36% |

The amount of free 2-ethylhexyl p-methoxycinnamate in the dispersion was 0.9315%.

The leaking speed of 2-ethylhexyl p-methoxycinnamate was 0.3521%/minute.

Reference Example 1

Production of N-[2-hydroxy-3-(3'-trihydroxysilyl)propoxy]propyl sodium polyaspartate A sodium polyaspartate solution (Aquadew SPA-30 manufactured by Ajinomono Co., Inc.) is electrically dialyzed, then, the concentration is controlled to 20% and the pH was controlled at about 11 to prepare a solution for reaction.

The prepared solution is charged into a glass reaction vessel, heated at 60° C. and stirred. When the reaction solution reaches 60° C., γ-glycidoxypropyltrimethoxysilane (KBE-403 manufactured by Shin-Etsu Silicone Co., Ltd.) is added dropwise from a dropping funnel and the mixture is stirred for 5 hours at 60° C. (the amount of the γ-glycidoxypropyltrimethoxysilane used is about 3.1 g per 100 g of the reaction solution).

The effective component concentration of the reacted compound is controlled to 15%.

Example 37

Production of a microcapsule containing 2-ethylhexyl p-methoxycinnamate and tetraethylsilane and having a capsule wall made of organopolysiloxane composed of a co-polycondensate of the hydrolysate of N-[2-hydroxy-3-(3'-trihydroxysilyl)propoxy]propyl sodium polyaspartate, methyltriethoxysilane, phenyltriethoxysilane and tetraethoxysilane.

1) Preparation of Prepolymer of Capsule Wall

A 2-liter round bottom cylindrical glass reaction vessel having an internal diameter of 12 cm was previously charged 90 g of water, 10 g of N-[2-hydroxy-3-(3'-trihydroxysilyl)propoxy]propyl sodium polyaspartate (number-average molecular weight of the sodium polyaspartate is about 1000), obtained in Reference Example 1, and 10 g of 18% hydrochloric acid, and a mixture of 12.3 g of methyltriethoxysilane (KBE-13 manufactured by Shin-Etsu Silicone Co., Ltd.), 3.3 g of phenyltriethoxysilane (KBE-103 manufactured by Shin-Etsu Silicone Co., Ltd.) and 1.9 g of tetraethoxysilane was dropped from the dropping funnel at 50° C. with stirring.

The mixture was further stirred for 4 hours at 55° C., then cooled to 25° C. Then, 10 g of a 20% aqueous sodium hydroxide solution was added dropwise, to control the pH to 7.0.

2) Addition of Core Material and Emulsification

A mixture of 160.7 g of 2-ethylhexyl p-methoxycinnamate (MCX, manufactured by Nippon Roche K.K.) and 1.6 g of tetraethoxysilane (KBE-04 manufactured by Shin-Etsu Silicone Co., Ltd.) was added thereto with stirring at 600 rpm, and the mixture was further stirred for 2 hours at 600 rpm.

3) Micronization

The reaction solution prepared in the process 2) was transferred to a vessel of a homomixer, and treated by the homomixer at 50° C. and 6000 rpm for 90 minutes to micronize the components.

4) Over Coat Treatment of Capsule Wall

A mixture of 0.3 g of methyltrichlorosilane (KA-13 manufactured by Shin-Etsu Silicone Co., Ltd.) and 6 g of methyltriethoxysilane (KBE-13 manufactured by Shin-Etsu Silicone Co., Ltd.) was added to the reaction solution prepared in the process 3) in the original reaction vessel with stirring at 50° C. and 450 rpm and the resulting mixture was stirred at 450 rpm for 1 more hour. Then 0.4 g of a 20% aqueous sodium hydroxide solution was added for neutralization.

5) Prevention of Coagulation and Curing Treatment of Capsule Wall 0.5 g of trimethylchlorosilane (KA-31, manufactured by Shin-Etsu Silicone Co., Ltd.) was added to the solution prepared in the process 4) with stirring at 450 rpm and 50° C., then, 0.6 g of a 20% aqueous sodium hydroxide solution was added dropwise after stirring at 450 rpm for 1 hour. The temperature of the reaction solution was raised gradually to reflux. A vapor containing alcohol was distilled off, and the remaining mixture was further heated to reflux with stirring at 150 rpm for 3 hours. This reaction solution was cooled with stirring at 150 rpm at room temperature to obtain a microcapsule containing core material.

The dispersion of the resulting microcapsule containing core material was analyzed according to Analysis methods 5 and 7 giving the following results.

| | |
|---|---|
| Water dispersion of a capsule having a diameter of 15 μm or smaller | |
| Components excepting water | 50.50% |

Analysis Method 8
Measurement of SPF Value and Ultraviolet Ray Transmittance

A measuring sample was applied on a surgical tape (TRANSPORE TAPE, manufactured by 3M Corp.), this was irradiated with a ultraviolet ray, and the amount of the transmitted light was measured by a SPF analyzer, (UV-1000S, manufactured by LABSPHERE Corp., US). The numerical value in the examples is an average of 40 values. The amount of the sample applied on a surgical tape is 2 μl/cm$^2$ and a certain amount when measuring SPF value and ultraviolet ray transmittance, respectively.

Calculation of SPF value $$SPF = \sum_{290\,nm}^{400\,nm} E(\lambda)\varepsilon(\lambda) \left/ \left[ \sum_{290\,nm}^{400\,nm} (E(\lambda)\varepsilon(\lambda))/(MFP(\lambda)) \right] \right.$$

E (λ): Spectral Distribution of Day Light
ε(λ): Action spectrum of delayed type actinic erythema
MPF (λ): Reciprocal of transmittance at each wavelength Analysis Method 9
Measurement of Skin Permeability Yucatan Micropig skin (5 months old, male, Nippon Charsliver) frozen and stored at −80° C. was thawed at room temperature over 30 minutes, effluent fat adhered to skin was removed, then, the skin was cut into 2 cm square and used for measurement. A sample was applied to thus obtained skin and subjected to permeation test.

The permeation test was conducted using an improved Franz type diffusion cell (area on which a preparation is applied is 1.1 cm$^2$, receptor phase: 16 ml). 0.1 ml of the prepared sample was placed into the donor phase, and kept at 37° C. for 24 hours. After 24 hours, the sample on the surface of the skin was cleanly removed by purified water, then, separated to epidemis and hypodemis. They were homogenized with 5 ml of MeOH, when, centrifugally separated (3000 rpm, 30 minutes), and the supernatant was separated and filtrated through a membrane filter (Cellulose Acetate 0.80 μm ADAVANTEC TOYO). Then, the concentration of the ultraviolet ray absorber was measured by HPLC.

[Measuring Condition of HPLC]

HPLC: Shimadzu LC-6A system (manufactured by Shimadzu Corp.)

Column: TSK-GEL ODS-120T 4.6 mm 150 mm (manufactured by Tosoh Corp.)

Mobile phase: methanol:water=9:1

Flow rate: 1.0 ml/min

Detector: Ultraviolet spectrophotometer SPD-6A (manufactured by Shimadzu Corp.)

Detection wavelength: 310 nm

Example 38

Ultraviolet ray transmittance at wave-length of 310 nm of samples obtained in Examples 22A, 24 and 28 and 2-ethylhexyl p-methoxycinnamate were measured according to Analysis method 8, and the results are shown in the following Table.

|  | Example 22A | Example 24 | Example 28 | 2-ethylhexyl p-methoxy-cinnamate |
|---|---|---|---|---|
| Applied amount 1 *1 | 54.1 | 61.1 | 64.5 | 72.2 |
| Applied amount 2 *2 | 48.7 | 54.5 | 58.1 | 72.2 |
| Ultraviolet ray transmittance | 1.7 | 1.0 | 1.75 | 2.2 |

*1 Applied amount 1: amount (mg) of the applied sample after dried on 80 cm² of the Tape
*2 Applied amount 2: amount (mg) of ultraviolet ray absorber contained in the applied sample on 80 cm² of the Tape.

Although the amounts of the applied samples obtained in Examples 22A, 24 and 28 are less than the amount of the applied 2-ethylhexyl p-methoxy-cinnamate, ultraviolet ray transmittance of the Examples 22A, 24 and 28 are smaller than that of 2-ethylhexyl p-methoxy-cinnamate.

Example 39

Skin permeability of a microcapsule obtained in Examples 28 and 50% by weight of isopropylmiristate solution of 2-ethylhexyl p-methoxycinnamate were measured according to Analysis method 9, and the results are shown in the following Table.

|  | Concentration in epidermis (μg/cm³) | Concentration in hypodermis (μg/cm³) |
|---|---|---|
| Microcapsule obtained in Examples 28 | 5 | 1700 |
| 2-Ethylhexyl p-methoxycinnamate/ isopropylmiristate solution | 52 | 12000 |

It was recognized that the microcapsule obtained in Examples 28 repress permeation into skin of a ultraviolet ray absorber contained in the capsule.

Example 40

Comparative Example 4

Liquid Foundation

Stearic acid, beeswax, hydrogenated lanolin, isopropyl isostearate, squalane and sorbitan sesquioleate were weighed, and dissolved at 80° C. (Solution 1). Separately, triethanolamine, 1,3-butylene glycol, partial purified water and the microcapsule containing core material obtained in the Example 13 were weighed, and heated to 85° C. and added to Solution 1 gradually with stirring. After cooling to 45° C., a perfume was added and cooled to about 40° C. (Solution 2).

Separately, titanium oxide, zinc oxide, kaolin, talc and iron oxide were weighed and to this was added the remaining purified water. The mixture was dispersed completely in a homomixer, then, Solution 2 was added thereto and the mixture was further stirred and dispersed thoroughly to obtain a sample for Example 40.

A sample for Comparative Example 4 was obtained in the same manner except 2-ethylhexyl p-methoxycinnamate was used instead of the microcapsule containing core material.

The amount of 2-ethylhexyl p-methoxycinnamate, a ultraviolet ray absorber, contained in the microcapsule used in the Example is same to that of the ultraviolet ray absorber compounded in the Comparative example. This will also be applied to the following examples and comparative examples.

Any of the amounts compounded of components in the examples and comparative examples is by weight, and when the amount compounded is not amount of a solid component, the concentration of the solid component is described in parenthesis following the component name. This will also be applied to the following examples and comparative examples.

|  |  | Amount compounded (W/W %) | |
|---|---|---|---|
|  |  | Example 40 | Comparative example 4 |
| 1 | Titanium oxide | 0.60 | 0.60 |
| 2 | Zinc oxide | 2.00 | 2.00 |
| 3 | Kaolin | 3.00 | 3.00 |
| 4 | Talc | 4.00 | 4.00 |
| 5 | Iron oxide | 1.00 | 1.00 |
| 6 | Stearic acid | 2.00 | 2.00 |
| 7 | Beeswax | 1.20 | 1.20 |
| 8 | Hydrogenated lanolin | 1.00 | 1.00 |
| 9 | Isopropyl isostearate | 2.00 | 2.00 |
| 10 | Squalane | 2.00 | 2.00 |
| 11 | Sorbitan sesquioleate | 0.40 | 0.40 |
| 12 | Triethanolamine | 0.50 | 0.50 |
| 13 | 1,3-Butylene glycol | 2.80 | 2.80 |
| 14 | Lecithin | 0.20 | 0.20 |
| 15 | Preservative | 0.30 | 0.30 |
| 16 | Perfume | 0.50 | 0.50 |
| 17 | Purified water | to make 100 | to make 100 |
| A | Microcapsule | 62.60 | — |
| B | 2-Ethylhexyl p-methoxycinnamate | — | 30.00 |

SPF value of the resulting liquid foundation was measured by Analysis method 8, and the results are shown below.

|  | SPF value |
|---|---|
| Example 40 | 20.8 |
| Comparative example 4 | 18.8 |

The appearance immediately after preparation and three months are shown below.

|  | Appearance (directly after preparation) | Appearance (after three months) |
|---|---|---|
| Example 40 | Uniform | Uniform |
| Comparative example 4 | Uniform | Coagulated, Separated |

The liquid foundation of Example 40 was superior to that of Comparative Example 4 in effect for preventing a ultraviolet ray. In spite of a large amount of 2-ethylhexyl p-methoxycinnamate compounded, coagulation and separation with the lapse of time did not occur, that is, stability was excellent. Further, when the liquid foundation of Example 40 was applied to skin, oil feeling was little and tackiness was repressed.

Example 41

Comparative Example 5

Solid foundations having the following formulations were obtained in analogous manners as in Example 40 and Comparative Example 4 using a microcapsule containing core material obtained in Example 22A.

|  |  | Amount compounded (W/W %) | |
|---|---|---|---|
|  |  | Example 41 | Comparative example 5 |
| 1 | Titanium oxide | 20.00 | 20.00 |
| 2 | Zinc oxide | 3.00 | 3.00 |
| 3 | Kaolin | 6.00 | 6.00 |
| 4 | Talc | 8.00 | 8.00 |
| 5 | Iron oxide | 4.00 | 4.00 |
| 6 | Beeswax | 8.40 | 8.40 |
| 7 | Polyoxyethylene curing castor oil | 0.60 | 0.60 |
| 8 | Carnauba wax | 1.20 | 1.20 |
| 9 | Olive oil | 13.50 | 13.50 |
| 10 | Purified castor oil | 6.00 | 6.00 |
| 11 | Sodium oleylphosphate | 0.60 | 0.60 |
| 12 | Preservative | 0.30 | 0.30 |
| 13 | Perfume | 0.30 | 0.30 |
| 14 | octyldodecanol | to make 100 | to make 100 |
| A | Microcapsule | 16.5 | — |
| B | 2-Ethylhexyl p-methoxycinnamate | — | 10.00 |

SPF value of a sample prepared by diluting the resulting solid foundation by 4-fold with octyldodecanol was measured by analysis method 8, and the results are shown below.

|  | SPF value |
|---|---|
| Example 41 | 16.7 |
| Comparative example 5 | 14.0 |

The product was applied in an amount of 0.5 g on the back of hand, and "adhesion to skin" was evaluated by 10 panelists, the results are shown below.

| Evaluation of adhesion | |
|---|---|
| Number of panelists who decided the product of Example 41 good | 7 |
| Number of panelists who decided the product of Comparative Example 5 good | 3 |

The solid foundation of Example 41 was superior to that of Comparative Example 5 in adhesion onto skin.

Example 42

Comparative Example 6

Sunscreen lotions having the following formulations were obtained in analogous manners as in Example 40 and Comparative Example 4 using a microcapsule containing core material obtained in Example 36.

|  |  | Amount compounded (W/W %) | |
|---|---|---|---|
|  |  | Example 42 | Comparative example 6 |
| 1 | Alkyl acrylate-alkyl methacrylate-polyoxyethylene (20) stearyl ether copolymerized emulsion (30%) | 0.60 | 0.60 |
| 2 | Hydroxyethyl-cellulose | 0.30 | 0.30 |
| 3 | Purified water | 20.00 | 20.00 |
| 4 | Sodium hydroxide (1% aqueous solution) | 3.00 | 3.00 |
| 5 | Purified water | 20.00 | 20.00 |
| 6 | Propylene glycol | 8.00 | 8.00 |
| 7 | EDTA-2Na | 0.20 | 0.20 |
| 8 | Preservative | 0.30 | 0.30 |
| 9 | Purified Water | to make 100.00 | to make 100.00 |
| A | Microcapsule | 9.4 | — |
| B | 2-Ethylhexyl p-methoxycinnamate | — | 4.00 |
| C | 4-tert-Butyl-4'-methoxydibenzoyl | — | 1.00 |

The resulting sunscreen lotion could not easily form a uniform coating when used in small amount, therefore, double amount (4 $\mu$l/cm$^2$) based on usual was used for the test. SPF value, UVA transmittance and UVB transmittance obtained by Analysis method 8 are shown below.

|  | SPF value | UVA transmittance (%) | UVB transmittance (%) |
|---|---|---|---|
| Example 42 | 10.7 | 33.1 | 7.6 |
| Comparative example 6 | 7.7 | 43.6 | 10.6 |

From the above-described results, it is apparent that the sunscreen lotion of Example 42 is excellent in ultraviolet ray preventing effect.

Appearance immediately after preparation and after three months are shown below.

|  | Appearance (immediately after preparation) | Appearance (after three months) |
|---|---|---|
| Example 42 | uniform emulsification | uniform emulsification |
| Comparative example 6 | rough emulsification and semitransparent | separated |

As a result of observation of change with the lapse of time, the product of Example 42 can be compounded stably even in a formulation system in which an active agent is not compounded as described above.

Example 43

Comparative Example 7

Sunscreen creams having the following formulations were obtained in analogous manners as in Example 40 and Comparative Example 4 using a microcapsule containing core material obtained in Example 36.

|  |  | Amount compounded (W/W %) | |
|---|---|---|---|
|  |  | Example 43 | Comparative example 7 |
| 1 | Alkyl acrylate-alkyl methacrylate-polyoxyethylene (20) stearyl ether copolymerer emulsion (30%) *1 | 1.00 | 1.00 |
| 2 | Carboxyvinyl polymer *2 (1% aqueous solution) | 50.00 | 50.00 |
| 3 | Cetostearyl 2-ethylhexanoate (2) | 5.00 | 5.00 |
| 4 | Concentrated glycerin | 3.00 | 3.00 |
| 5 | EDTA-2Na | 0.20 | 0.20 |
| 6 | Preservative | 0.20 | 0.20 |
| 7 | Triethanolamine | 1.30 | 1.30 |
| 8 | Purified water | 10.00 | 10.00 |
| 9 | Purified water | to make 100.0 | to make 100.0 |
| A | Microcapsule | 18.7 | — |
| B | 2-Ethylhexyl p-methoxycinnamate | — | 8.00 |
| C | 4-tert-Butyl-4'-methoxydibenzoyl | — | 2.00 |

*1 Aculyn 22 (manufactured by ROHM and HAAS)
*2 Carbopole 940 (manufactured by The BF Goodrich Company)

SPF value, UVA transmittance and UVB transmittance of the resulting sunscreen cream are shown below. In Comparative Example 7, the product was separated and not uniform, therefore, sampling was effected immediately after intense stirring and the resulting samples were subjected to the tests.

|  | SPF value | UVA transmittance (%) | UVB transmittance (%) |
|---|---|---|---|
| Example 43 | 4.7 | 50.9 | 19.0 |
| Comparative example 7 | 3.8 | 56.2 | 23.7 |

Appearance immediately after preparation and after three months are shown below.

|  | Appearance (immediately after preparation) | Appearance (after three months) |
|---|---|---|
| Example 43 | uniform emulsification | uniform emulsification |
| Comparative example 7 | separated | separated |

As is known from the above-described results, microcapsule of the instant invention can be easily compounded in a formulation, and is excellent in stability with the lapse of time. Therefore, compounding of a ultraviolet ray absorber became possible even in cosmetics in which compounding of a ultraviolet ray absorber has been conventionally difficult.

Example 44

Comparative Example 8

Milky lotions having the following formulations were obtained in analogous manners as in Example 40 and Comparative Example 4 using a microcapsule containing core material obtained in Example 28.

|  |  | Amount compounded (W/W %) | |
|---|---|---|---|
|  |  | Example 44 | Comparative example 8 |
| 1 | Polyoxyethylene (10) curing castor oil | 5.00 | 5.00 |

-continued

| | | Amount compounded (W/W %) | |
|---|---|---|---|
| | | Example 44 | Comparative example 8 |
| 2 | Isopropyl myristate | 6.00 | 6.00 |
| 3 | Liquid paraffin #70 | 5.00 | 5.00 |
| 4 | Jojoba oil | 5.00 | 5.00 |
| 5 | Magnesium stearate | 0.80 | 0.80 |
| 6 | Zinc oxide | 3.00 | 3.00 |
| 7 | Magnesium sulfate | 0.30 | 0.30 |
| 8 | conc. Glycerine | 5.00 | 5.00 |
| 9 | EDTA-2Na | 0.10 | 0.10 |
| 10 | Tocopherol acetate | 1.00 | 1.00 |
| 11 | Preservative | 0.30 | 0.30 |
| 12 | Purified water | to make 100 | to make 100 |
| A | Microcapsule | 16.5 | — |
| B | 2-Ethylhexyl p-methoxycinnamate | — | 10.00 |

SPF value of the resulting milky lotion was measured by analysis method 8, and the results are shown below.

| | SPF value |
|---|---|
| Example 44 | 15.7 |
| Comparative example 8 | 12.4 |

The product was applied in an amount of 0.5 g on the back of hand, and "adhesion to skin" was evaluated by 10 panelists, the results are shown below.

| Evaluation of adhesion | |
|---|---|
| Number of panelists who decided the product of Example 44 not good | 3 |
| Number of panelists who decided the product of Comparative Example 8 not good | 7 |

The milky lotion of Example 44 was superior to that of Comparative Example 8 in adhesion onto skin.

Example 45

Comparative Example 9

Sunscreen creams having the following formulations were obtained in an analogous manners to that in Example 40 and Comparative Example 4 using a microcapsule containing core material obtained in Example 13.

| | | Amount compounded (W/W %) | |
|---|---|---|---|
| | | Example 45 | Comparative example 9 |
| 1 | Stearic acid | 2.5 | 2.5 |
| 2 | Cetanol | 1.5 | 1.5 |
| 3 | Vaseline | 5.0 | 5.0 |
| 4 | Liquid paraffin #70 | 10.0 | 10.0 |
| 5 | Polyoxyethylene (20) oleyl ether | 2.0 | 2.0 |

-continued

| | | Amount compounded (W/W %) | |
|---|---|---|---|
| | | Example 45 | Comparative example 9 |
| 6 | Preservative | 0.3 | 0.3 |
| 7 | Polyethyleneglycol4000 | 3.0 | 3.0 |
| 8 | Triethanol amine | 2.0 | 2.0 |
| 9 | Purified water | to make 100 | to make 100 |
| A | Microcapsule | 41.70 | — |
| B | 2-Ethylhexyl p-methoxycinnamate | — | 20.00 |

SPF value of the resulting sunscreen cream was measured by Analysis method 8, and the results are shown below.

| | SPF value |
|---|---|
| Example 45 | 12.5 |
| Comparative example 9 | 11.5 |

Appearance immediately after preparation and after six months are shown below.

| | Appearance (immediately after preparation) | Appearance (after six months) |
|---|---|---|
| Example 45 | uniform emulsification, white | uniform emulsification, white |
| Comparative example 9 | uniform emulsification, white | separated become yellowish |

As is known from the above-described results, the microcapsule is excellent in stability with the lapse of time and prevents yellow coloration of the cream composition.

Example 46

Comparative Example 10

Hair treatments having the following formulations were obtained in analogous manners as in Example 40 and Comparative Example 4 using a microcapsule containing core material obtained in Example 22A.

| | | Amount compounded (W/W %) | |
|---|---|---|---|
| | | Example 46 | Comparative example 10 |
| 1 | Mixture of polyacrylamide, polyoxyethylene-solbitoltrioleinate, liquid paraffin and volatile isoparaffin | 2.0 | 2.0 |
| 2 | Copolymer of poly (oxyethylene, oxypropylene) and methylpolysiloxane | 5.0 | 5.0 |

-continued

| | | Amount compounded (W/W %) | |
|---|---|---|---|
| | | Example 46 | Comparative example 10 |
| 3 | 22-Ethylhexyl isoparmitate | 2.0 | 2.0 |
| 4 | Chlorinated N-[2-hydroxy-3-(palm oil alkyldimethylammonio)propyl] hydrolized collagen | 0.3 | 0.3 |
| 11 | Preservative | 0.3 | 0.3 |
| 12 | Purified water | to make 100 | to make 100 |
| A | Microcapsule | 4.9 | — |
| B | 2-Ethylhexyl p-methoxycinnamate | — | 3.0 |

SPF value of the resulting hair treatment was measured by Analysis method 8, and the results are shown below.

| | SPF value |
|---|---|
| Example 46 | 6.2 |
| Comparative example 10 | 5.6 |

The product was applied in an amount of 0.2 g on a 1 g of hair bundle rinsed previously, then the hair bundle was dried. Combability was evaluated by 10 panelists, the results are shown below.

| Evaluation of adhesion | |
|---|---|
| Number of panelists who decided the product of Example 46 good | 9 |
| Number of panelists who decided the product of Comparative Example 10 good | 1 |

The hair treatments of Example 46 was superior to that of Comparative Example 10 in combability.

Example 47

Comparative Example 11

Lipsticks having the following formulations were obtained in analogous manners as in Example 40 and Comparative Example 4 using a microcapsule containing core material obtained in Example 24.

| | | Amount compounded (W/W %) | |
|---|---|---|---|
| | | Example 47 | Comparative example 11 |
| 1 | Beeswax | 7.0 | 7.0 |
| 2 | Candelira wax | 10.5 | 10.5 |
| 3 | Methyl polysiloxane | 11.2 | 11.2 |
| 4 | Castor oil | 15.0 | 15.0 |
| 5 | Liquid paraffin #70 | 18.0 | 18.0 |
| 6 | Glycerin triisostearate | 15.0 | 15.0 |
| 7 | Mica | 10.0 | 10.0 |
| 8 | Iron oxide | 3.6 | 3.6 |
| 9 | Red No.2 | 0.2 | 0.2 |
| 10 | Purified water | to make 100 | to make 100 |
| A | Microcapsule | 5.2 | — |
| B | 2-Ethylhexyl p-methoxycinnamate | — | 3.0 |

SPF value of the sample prepared by dilluting the resulting lipstick by 2-fold with liquid paraffin was measured by Analysis method 8, and the results are shown below.

| | SPF value |
|---|---|
| Example 47 | 8.2 |
| Comparative example 11 | 7.8 |

The results show the lipsticks of Example 47 is excellent in ultraviolet ray preventing effect.

Example 48

Comparative Example 12

Creams having the following formulations were obtained in analogous manners as in Example 40 and Comparative Example 4 using a microcapsule containing core material obtained in Example 28.

| | | Amount compounded (W/W %) | |
|---|---|---|---|
| | | Example 48 | Comparative example 12 |
| 1 | Carboxyvinyl polymer | 0.30 | 0.30 |
| 2 | Potassium hydroxide | 0.15 | 0.15 |
| 3 | 1,3-Butylene glycol | 5.00 | 5.00 |
| 4 | Diglycerin | 2.00 | 2.00 |
| 5 | Tetrasodium hydroxyethane-diphosphonate | 0.09 | 0.09 |
| 6 | p-Oxybenzoate | 0.25 | 0.25 |
| 7 | Purified water | to make 100.0 | to make 100.0 |
| A | Microcapsule | 10.0 | — |
| B | 2-Ethylhexyl p-methoxycinnamate | — | 4.5 |

SPF value of the resulting cream was measured by Analysis method 8 and the results are shown below.

| | SPF value |
|---|---|
| Example 48 | 5.4 |
| Comparative example 12 | 5.0 |

The cream of Example 48 was excellent in ultraviolet ray preventing effect.

The skin permeability of the prepared product was measured by Analysis method 9 and the results are shown below.

|  | Concentration in epidermis ($\mu g/cm^3$) | Concentration in hypodermis ($\mu g/cm^3$) |
|---|---|---|
| Example 48 | 1,100 | 2.5 |
| Comparative example 12 | 4,900 | 50 |

It was recognized that the cream of example 48 repress permeation into skin of a ultraviolet ray absorber to be compounded.

What we claim is:

1. A microcapsule containing core material and a capsule wall, in which the capsule wall of the microcapsule comprises:

organopolysiloxane synthesized by polycondensing a compound (B) monomer or a compound (B) containing monomeric mixture, wherein the compound (B) contains one or more compounds represented by the general formula (II):

$$R_n Si(OH)_m Y_{(4-m-n)} \quad \text{(II)}$$

wherein, m represents an integer from 1 to 4; n represents an integer from 0 to 3; m+n≦4; R represents an organic group in which a carbon atom is directly connected to a silicone atom, and when n is greater than 1, each of the R groups may be the same or different; and Y represents at least one group selected from the group consisting of an alkoxy group, hydrogen and siloxy group, and when (4−m−n) is greater than 1, each of the groups Y may be the same or different; provided that the compound (B) comprises at least one compound of formula (II) wherein m=2 or 3 and at least one of R group carries a hydrolyzed protein.

2. The microcapsule containing core material according to claim 1, wherein the compound (B) is obtained by hydrolyzing a compound (A) monomer or a compound (A) containing monomeric mixture, wherein the compound (A) contains one or more compounds represented by the following general formula (I):

$$R_n SiX_{(4-n)} \quad \text{(I)}$$

wherein, n represents an integer from 0 to 3; R represents an organic group in which a carbon atom is directly connected to a silicone atom, and when n is greater than 1, each of the R groups may be the same or different; and X represents at least one group selected from the group consisting of a hydroxyl group, hydrogen, alkoxy group, halogen group, carboxyl group, amino group and siloxy group, and when (4−n) is greater than 1, each of the groups X may be the same or different; provided that the compound (A) contains at least one compound of formula (I) having an R group carrying a hydrolyzed protein.

3. The microcapsule containing core material according to claim 1, wherein the hydrolyzed protein group is an N-[2-hydroxy-3-(3'-trihydroxysilyl)propoxy]propyl hydrolyzed protein or an N-[2-hydroxy-3-(3'-dihydroxymethylsilyl)propoxy]propyl hydrolyzed protein.

4. The microcapsule containing core material according to claim 3, wherein each of the hydrolyzed proteins possesses a number-average molecular weight of from about 100 to 50000.

5. The microcapsule containing core material according to claim 1, wherein at least one compound selected from the group consisting of hydrolyzable silanes and hydrolyzable polysiloxanes is present in the core material of the microcapsule.

6. The microcapsule containing core material according to claim 1 wherein a surface of the capsule wall of the microcapsule is treated at least once, prior to a curing treatment, with a hydrolysate of at least one compound selected from the group consisting of hydrolyzable silanes and hydrolyzable polysiloxanes.

7. The microcapsule containing core material according to claim 1, wherein a surface of the capsule wall is treated, prior to a curing treatment, with a compound (A) monomer or a compound (A) containing monomeric mixture, wherein the compound (A) contains one or more compounds represented by the following general formula (I):

$$R_n SiX_{(4-n)} \quad \text{(I)}$$

wherein, n represents an integer from 0 to 3; R represents an organic group in which a carbon atom is directly connected to a silicone atom, and when n is greater than 1, each of the R groups may be the same or different; and X represents at least one group selected from the group consisting of a hydroxyl group, hydrogen, alkoxy group, halogen group, carboxyl group, amino group and siloxy group, and when (4−n) is greater than 1, each of the groups X may be the same or different; provided that the compound (A) contains at least one compound of formula (I) having an R group which possesses affinity for at least one of a continuous phase and a dispersed phase.

8. The microcapsule containing core material according to claim 5, wherein the at least one compound selected from the group consisting of hydrolyzable silanes and hydrolyzable polysiloxanes is methyltrichlorosilane, methyldichlorosilane, dimetyldichlorosilane, trimethylchlorosilane, phenyltrichlorosilane, diphenyldichlorosilane, methyltrimethoxysilane, methyltriethoxysilane, phenyltrimethoxysilane, phenyltriethoxysilane, diphenyldimethoxysilane, diphenyldiethoxysilane, hexyltrimethoxysilane, octyltriethoxysilane, decyltrimethoxysilane, tetramethoxysilane, tetraethoxysilane or $Me_3SiO(Me_2SiO)_f(MeZSiO)_g SiMe_3$, wherein f represents an integer from 5 to 50, and g represents an integer from 2 to 100 and Z represents hydrogen or an alkoxy group.

9. The microcapsule containing core material according to claim 6, wherein the at least one compound selected from the group consisting of hydrolyzable silanes and hydrolyzable polysiloxanes is methyltrichlorosilane, methyldichlorosilane, dimetyldichlorosilane, trimethylchlorosilane, phenyltrichlorosilane, diphenyldichlorosilane, methyltrimethoxysilane, methyltriethoxysilane, phenyltrimethoxysilane, phenyltriethoxysilane, diphenyldimethoxysilane, diphenyldiethoxysilane, hexyltrimethoxysilane, octyltriethoxysilane, decyltrimethoxysilane, tetramethoxysilane, tetraethoxysilane or $Me_3SiO(Me_2SiO)_f$ $(MeZSiO)_gSiMe_3$, wherein f represents an integer from 5 to 50, and g represents an integer from 2 to 100 and Z represents hydrogen or an alkoxy group.

10. The microcapsule containing core material according to claim 1, wherein the core material contains an ultraviolet absorber.

11. The microcapsule containing core material according to claim 10, wherein the ultraviolet absorber is 2-ethylhexyl p-methoxycinnamate or 4-tert-butyl-4'-methoxydibenzoylmethane.

12. An agent or preparation which comprises a microcapsule containing core material according to claim 10.

13. The agent or preparation according to claim 12 which is a cosmetic or a pharmaceutical preparation.

14. The agent or preparation according to claim 13 wherein said agent or preparation is applied to the skin or hair.

* * * * *